(12) United States Patent
Kataoka et al.

(10) Patent No.: US 10,046,065 B2
(45) Date of Patent: Aug. 14, 2018

(54) NUCLEIC ACID-ENCAPSULATING POLYMER MICELLE COMPLEX AND METHOD FOR PRODUCING SAME

(71) Applicant: JAPAN SCIENCE AND TECHNOLOGY AGENCY, Kawaguchi-shi, Saitama (JP)

(72) Inventors: Kazunori Kataoka, Tokyo (JP); Kensuke Osada, Tokyo (JP); Theofilus Agrios Tockary, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 14/909,162

(22) PCT Filed: Aug. 5, 2014

(86) PCT No.: PCT/JP2014/070567
§ 371 (c)(1),
(2) Date: Feb. 1, 2016

(87) PCT Pub. No.: WO2015/020026
PCT Pub. Date: Feb. 12, 2015

(65) Prior Publication Data
US 2016/0184457 A1   Jun. 30, 2016

(30) Foreign Application Priority Data
Aug. 6, 2013 (JP) ................... 2013-163106

(51) Int. Cl.
| | |
|---|---|
| B01L 3/00 | (2006.01) |
| C12Q 1/04 | (2006.01) |
| C12Q 1/68 | (2018.01) |
| A61K 48/00 | (2006.01) |
| A61K 47/34 | (2017.01) |
| A61K 9/00 | (2006.01) |
| A61K 9/107 | (2006.01) |
| C12N 15/88 | (2006.01) |
| A61K 31/711 | (2006.01) |
| A61K 31/713 | (2006.01) |

(52) U.S. Cl.
CPC ........ A61K 48/0041 (2013.01); A61K 9/0019 (2013.01); A61K 9/1075 (2013.01); A61K 47/34 (2013.01); A61K 48/0091 (2013.01); C12N 15/88 (2013.01); A61K 31/711 (2013.01); A61K 31/713 (2013.01); A61K 48/00 (2013.01)

(58) Field of Classification Search
CPC .... A61K 31/711; A61K 31/713; A61K 47/34; A61K 48/00; A61K 48/0041; A61K 48/0091; A61K 9/0019; A61K 9/1075; C12N 15/88
USPC .......... 424/497; 514/44 A; 435/458
See application file for complete search history.

(56) References Cited

U.S. PATENT DOCUMENTS

| | | | |
|---|---|---|---|
| 5,925,720 A | 7/1999 | Kataoka et al. | |
| 5,929,177 A | 7/1999 | Kataoka et al. | |
| 5,973,069 A | 10/1999 | Kataoka et al. | |
| 2010/0278927 A1* | 11/2010 | Mirosevich .......... | A61K 9/1075 424/497 |
| 2011/0052917 A1 | 3/2011 | Kataoka et al. | |

FOREIGN PATENT DOCUMENTS

| | | |
|---|---|---|
| JP | H08-188541 A | 7/1996 |
| JP | 2000-503645 A | 3/2000 |
| JP | 2010-233499 A | 10/2010 |
| JP | 2011-010549 A | 1/2011 |
| JP | 2011-105792 A | 6/2011 |
| JP | 2012-197323 A | 10/2012 |
| WO | 96/32434 A1 | 10/1996 |
| WO | 96/33233 A1 | 10/1996 |
| WO | 97/06202 A1 | 2/1997 |
| WO | 97/25067 A2 | 7/1997 |
| WO | 2004/105799 A1 | 12/2004 |
| WO | 2006/118260 A1 | 11/2006 |
| WO | 2009/113645 A1 | 9/2009 |

OTHER PUBLICATIONS

European Patent Office, "Extended European Search Report," issued in European Patent Application No. 14 835 1224, which is a European Counterpart of U.S. Appl. No. 14/909,162, dated Jun. 9, 2016, 6 pages.
Kensuke Osada et al., "Enhanced gene expression promoted by the quantized folding of pDNA within polyplex micelles", Biomaterials, vol. 33, pp. 325-332 (2012).
Qixian Chen et al., "Homo-catiomer integration into PEGylated polyplex micelle from block-catiomer for systemic anti-angiogenic gene therapy for fibrotic pancreatic tumors", Biomaterials, vol. 33, pp. 4722-4730 (2012).
Hirokuni Uchida et al., "Odd-even effect of repeating aminoethylene units in the side chain of N-substituted polyaspartamides on gene transfection profiles", Journal of the American Chemical Society, vol. 133 (39), 15524-15532 (2011).

(Continued)

*Primary Examiner* — Janet L Epps-Smith
(74) *Attorney, Agent, or Firm* — Amster, Rothstein & Ebenstein LLP

(57) ABSTRACT

A nucleic acid-encapsulating polymer micelle complex is formed of a block copolymer containing an uncharged hydrophilic polymer chain block and a cationic polymer chain block; and two single-stranded DNA molecules having mutually complementary base sequences of 1000 or more bases in length, double-stranded DNA of 1000 or more base pairs in length in which at least a part of a double helix structure is dissociated and forms a single-stranded structure, or one single-stranded DNA molecule of 1000 or more bases in length.

9 Claims, 9 Drawing Sheets

(56) References Cited

OTHER PUBLICATIONS

Zhishen Ge et al., "Targeted gene delivery by polyplex micelles with crowded PEG palisade and cRGD moiety for systemic treatment of pancreatic tumors", Biomaterials, vol. 35 (10), pp. 3416-3426 (Mar. 2014).
International Search Report received for PCT Patent Application No. PCT/JP2014/070567 dated Oct. 28, 2014, with English Translation, 2 pages.
Kazunori Kataoka et al., "Spontaneous Formation of Polyion Complex Micelles with Narrow Distribution from Antisense Oligonucleotide and Cationic Block Copolymer in Physiological Saline", Macromolecules, vol. 29 (26), pp. 8556-8557 (1996).

* cited by examiner

NUCLEIC ACID-ENCAPSULATING POLYMER MICELLE COMPLEX AND METHOD FOR PRODUCING SAME

CROSS-REFERENCE TO RELATED APPLICATIONS

This application is a U.S. national stage entry under 35 U.S.C. § 371 of PCT International Patent Application No. PCT/JP2014/070567, filed Aug. 5, 2014, which claims the benefit of Japanese Patent Application No. 2013-163106, filed Aug. 6, 2013, the contents of which are incorporated herein by reference into the subject application.

TECHNICAL FIELD

The present invention relates to a polymer micelle complex encapsulating a nucleic acid (DNA). More specifically, the present invention relates to a polymer micelle complex which is sufficiently small in spite of encapsulation of relatively long-chain DNA.

Priority is claimed on Japanese Patent Application No. 2013-163106, filed Aug. 6, 2013, the content of which is incorporated herein by reference.

BACKGROUND ART

As a next-generation treatment, gene therapy for treating diseases by controlling gene expression has been greatly anticipated. The biggest problem with gene therapy is that introduction efficiency at the time when genes are introduced into target cells or tissues is insufficient. Particularly, in order to realize gene therapy through systemic administration, it is necessary that genes be stably circulated in the blood and accumulated on target tissues and that gene expression be effectively performed after genes have entered target tissues. Here, in order to solve these problems, development of gene carriers having better introduction efficiency to target cells or the like, and gene expression efficiency in target cells has been actively promoted.

For example, it is known that a polymer in which a primary structure is precisely controlled is spontaneously organized and may form a higher-order structure such as a micelle or a vesicle and use of a structure obtained by a polymer being self-organized in such a manner has been previously examined in various fields including drug delivery systems and material science. For example, PTL 1 discloses an electrostatic binding type polymer micelle drug carrier formed of a block copolymer including an uncharged segment (uncharged polymer chain block) and a charged segment (charged polymer chain block) and capable of encapsulating a drug having an opposite charge to that of the charged segment, in a core portion. When a cationic segment is used as the charged segment, it is possible to encapsulate DNA in the core portion.

Furthermore, research performed for stabilization of a polymer micelle in various manners has been reported. For example, in regard to an electrostatic binding type polymer micelle drug carrier, PTL 2 discloses an electrostatic binding type polymer micelle drug carrier stabilized by crosslinking block copolymers through a crosslinking agent. In addition, PTL 3 discloses a block copolymer formed by containing an uncharged hydrophilic polymer chain block and a cationic polyamino acid chain block in which a hydrophobic group is introduced into a part of the side chain thereof. By virtue of a hydrophobic group introduced into the side chain of the block copolymer, interfacial energy is increased, thereby the cohesive force in a micelle becomes higher and the core becomes smaller, and thus, the polymer micelle is stabilized.

CITATION LIST

Patent Literature

[PTL 1] Japanese Unexamined Patent Application, First Publication No. H8-188541
[PTL 2] PCT International Publication No. WO2004/105799
[PTL 3] PCT International Publication No. WO2009/113645

SUMMARY OF INVENTION

Technical Problem

In a case where a gene carrier is systemically administered, it is necessary that the gene carrier have high retention in blood in order to introduce genes into a target cell.

Furthermore, when the size of the gene carrier is extremely large, there is a problem in that genes are unlikely to be introduced to a cell. Particularly in a case of cancers with low vascular density such as pancreatic cancer, the permeability of blood vessels becomes a barrier, and thus, it is extremely difficult for a gene carrier having a size of 100 nm to be delivered to a deep portion of cancer tissue through systemic administration.

Although a polymer micelle complex in which genes are accommodated in a core of an electrically binding type polymer micelle drug carrier is extremely promising as a gene carrier, there is still room for improvement in terms of size and retention in blood.

The main purpose of the present invention is to provide a polymer micelle complex which encapsulates relatively long-chain DNA, has a sufficiently small size, and is capable of functioning as a gene carrier, and a method for producing the same.

Solution to Problem

With regard to a polymer micelle complex in which a block copolymer formed of polyethylene glycol (PEG), which is a biocompatible neutral polymer, and a cationic polymer (hereinafter, also referred to as a "cationic polymer chain block") encapsulates Plasmid DNA (hereinafter, also referred to as "pDNA"), which is circular double-stranded DNA, the present inventors investigated a relationship between the length of the cationic polymer chain block (polymerization degree) and the particle diameter of the polymer micelle complex. The present inventors found there is a tendency that, in a case where the length of the cationic polymer chain block is relatively small, the polymer micelle complex becomes a rod shape having a length of 100 nm or greater in a long axis. On the other hand, the length of the long axis becomes smaller as the length of the cationic polymer chain block becomes greater, and in the case where the length of the cationic polymer chain block becomes sufficiently greater, the polymer micelle complex becomes smaller such that the shape thereof is close to a spherical shape as In addition, when the present inventors examined a relationship between the PEG density and the retention time in blood, they found that there is a tendency that the higher the PEG density of the polymer micelle complex is, the longer the retention time of the polymer micelle complex in blood becomes. Here, as the length of the cationic polymer chain block becomes shorter, the number of block copolymers that are associated with one pDNA molecule becomes smaller, and thus, the PEG density is lowered. That is, in a case of the polymer micelle complex encapsulating pDNA, it is understood that the retention in blood decreases when the PEG density is lowered in order to reduce the particle diameter.

As a result of additional research conducted by the present inventors, they found that, when a complex is formed by mixing pDNA into a block copolymer in a state where a double helix structure of the pDNA is dissociated, a polymer micelle complex in a spherical shape which is far smaller than a rod shape can be formed without lowering the density of an uncharged hydrophilic polymer chain block constituting a shell portion. Thereby the present inventors accomplished the present invention.

That is, a nucleic acid-encapsulating polymer micelle complex of the present invention and a method for producing the same are as described in [1] to [15] below.

[1] A nucleic acid-encapsulating polymer micelle complex formed of a block copolymer containing an uncharged hydrophilic polymer chain block and a cationic polymer chain block; and two single-stranded DNAs having mutually complementary base sequences of 1000 or more bases in length, double-stranded DNA of 1000 or more base pairs in length, in which at least a part of a double helix structure is dissociated and forms a single-stranded structure, or one single-stranded DNA of 1000 or more bases in length.

[2] The nucleic acid-enapsulating polymer micelle complex according to [1], formed of a block copolymer containing an uncharged hydrophilic chain block and a cationic polymer chain block; and two single-stranded DNAs having mutually complementary base sequences of 1000 or more bases in length or double-stranded DNA of 1000 or more base pairs in length in which at least a part of a double helix structure is dissociated and forms a single-stranded structure.

[3] The nucleic acid-encapsulating polymer micelle complex according to [1] or [2], in which the single-stranded DNA is 2000 or more bases in length, and the double-stranded DNA is 2000 or more base pairs in length.

[4] The nucleic acid-encapsulating polymer micelle complex according to any one of [1] to [3], in which the average particle diameter thereof in an aqueous medium measured according to a dynamic light scattering method is 100 nm or less.

[5] The nucleic acid-encapsulating polymer micelle complex according to any one of [1] to [4], in which the DNA and the cationic polymer chain block bonded to the DNA due to an electrostatic interaction form a core portion, and the uncharged hydrophilic polymer chain block forms a shell portion.

[6] The nucleic acid-encapsulating polymer micelle complex according to [5], in which the average particle diameter of the core portion is 50 nm or less.

[7] The nucleic acid-encapsulating polymer micelle complex according to any one of [1] to [6], in which the complex is spherical.

[8] The nucleic acid-encapsulating polymer micelle complex according to any one of [1] to [7], in which the single-stranded DNA or the double-stranded DNA is linear.

[9] The nucleic acid-encapsulating polymer micelle complex according to any one of [1] to [8], in which at least a part of the block copolymer is mutually cross-linked.

[10] The nucleic acid-encapsulating polymer micelle complex according to any one of [1] to [9], in which a hydrophobic group is covalently bonded to a main chain or a side chain of the cationic polymer chain block.

[11] The nucleic acid-encapsulating polymer micelle complex according to any one of [1] to [10], in which the cationic polymer chain block has an ethylamine structure or a propylamine structure in the side chain thereof.

[12] A method for producing a nucleic acid-encapsulating polymer micelle complex which accommodates DNA, the method comprising: a process of mixing a block copolymer containing an uncharged hydrophilic polymer chain block and a cationic polymer chain block with double-stranded DNA of 1000 or more base pairs in a state in which at least a part of a double helix structure is dissociated, in an aqueous medium.

[13] The method for producing a nucleic acid-encapsulating polymer micelle complex according to [12], in which the double-stranded DNA is 2000 or more base pairs in length.

[14] The method for producing a nucleic acid-encapsulating polymer micelle complex according to [12] or [13], in which the double-stranded DNA is linear.

[15] The method for producing a nucleic acid-encapsulating polymer micelle complex according to any one of [12] to [14], in which the double-stranded DNA has been denatured at 60° C. or higher.

Advantageous Effects of Invention

According to the present invention, in a case where long-chain DNA of 1000 or more base pairs in length and preferably 2000 or more base pairs in length is included, it is possible to provide a spherical polymer micelle complex, even using a block copolymer which mainly formed a rod-like or toroidal nucleic acid-encapsulating polymer micelle complex in the past. Since in the spherical polymer micelle complex, the particle diameter thereof is smaller than that of a rod-like nucleic acid-encapsulating polymer micelle complex and the density of the uncharged hydrophilic polymer chain block constituting the block copolymer is also higher, efficiency of introduction into a cell and retention in blood are both excellent.

DESCRIPTION OF EMBODIMENTS

Figure 1:
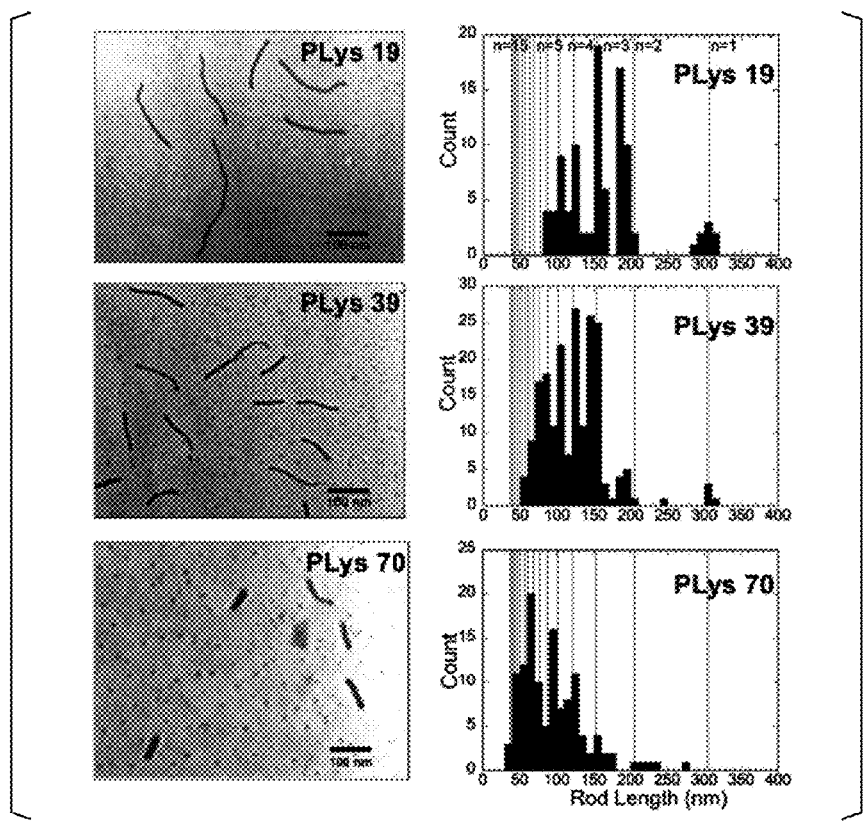
FIG. 1 shows TEM images of respective polymer micelle complexes in Reference Example 1 and diagrams of distribution of long axis lengths of polymer micelle complexes (rod-like particles) calculated from the images.

A nucleic acid-encapsulating polymer micelle complex according to the present invention is formed of a block copolymer containing an uncharged hydrophilic polymer chain block and a cationic polymer chain block; and a nucleic acid (DNA). The nucleic acid associated with the cationic polymer chain block forms a core portion, and the uncharged hydrophilic polymer chain block forms a shell portion. Hereinafter, the present invention will be described in detail.

<Uncharged Hydrophilic Polymer Chain Block>

The block copolymer used in the present invention contains an uncharged hydrophilic polymer chain block and a cationic polymer chain block. Examples of the uncharged hydrophilic polymer chain block include polyalkylene glycol such as PEG or polypropylene glycol; polyoxazoline such as poly(2-methyl-2-oxazoline), poly(2-ethyl-2-oxazoline), or poly(2-isopropyl-2-oxazoline); polysaccharides, dextran, polyvinyl alcohol, polyvinyl pyrrolidone, polyacrylamide, polymethacrylamide, polyacrylic acid ester, polymethacrylic acid ester, and various blocks derived from derivatives of these. Among these, from a viewpoint of a neutral water-soluble polymer having high biocompatibility, PEG, polyoxazoline, dextran, or polyvinyl alcohol is preferable.

The molecular weight of the uncharged hydrophilic polymer chain block may be in a level in which a block copolymer can form a polymer micelle complex in which a nucleic acid is accommodated and the molecular weight thereof is not particularly limited.

For example, in a case where a PEG-derived block (polyoxyethylene chain block, hereinafter, also simply referred to as a "PEG block") is used as an uncharged hydrophilic polymer chain block, the molecular weight of the PEG block is in a range of approximately 1.0 kDa to 100 kDa, more preferably in a range of 2 kDa to 80 kDa, and still more preferably in a range of 8 kDa to 25 kDa. Furthermore, the number of repeating units of oxyethylene in the PEG block is preferably in a range of 22 to 2300, more preferably in a range of 45 to 1850, and still more preferably in a range of 180 to 600.

<Cationic Polymer Chain Block>

As the cationic polymer chain block used in the present invention, a block formed of a cationic polymer chain which can be electrostatically bonded to DNA may be used, but the cationic polymer chain block is not particularly limited thereto. Specific examples thereof include a polyamino acid derivative having a cationic group in the side chain; polyethyleneimine (PEI), and an acrylic resin such as a polymethacrylic acid derivative or a polyacrylic acid derivative.

As the cationic polymer chain block used in the present invention, a block derived from a polyamino acid of a cationic amino acid or a derivative thereof or a block derived from an amino acid derivative in which a cationic compound is bonded to an anionic group (typically, a carboxyl group) of an anionic amino acid through an ester bond or an amide bond is preferably used. Examples of the polyamino acid of a cationic amino acid include polylysine, polyornithine, polyarginine, polyhomoarginine, and polyhistidine. Furthermore, as the amino acid derivative in which a cationic compound is bonded to an anionic amino acid, a derivative in which a compound including a cationic group such as an amino group, an imino group, or a quaternary amino group is bonded to a site other than a side in which a carboxyl group is bonded to one carboxyl group of aspartic acid or glutamic acid is exemplified. Examples of the compound including the cationic group include various diamines. A block having a repeating unit derived from an amino acid derivative obtained by reacting one of aspartic acid and glutamic acid with diethylenetriamine has an ethylamine structure in the side chain thereof. In addition, a block having a repeating unit derived from a polyamino acid derivative obtained by introducing a propylamine structure in the side chain is preferable.

In the present invention, it is particularly preferable to use a block copolymer having, as a cationic polymer chain block, a block which has a repeating unit of lysine and/or a derivative thereof and is derived from a polyamino acid (hereinafter, also referred to as a "PLys block") or a block which has a repeating unit of an amino acid derivative in which diethylenetriamine is bonded to one carboxyl group of aspartic acid and/or a derivative thereof and is derived from a polyamino acid (hereinafter, also referred to as a "PAsp (DET) block").

Since the density of the uncharged hydrophilic polymer chain block that forms a shell can easily be set to be high when the block copolymer forms a polymer micelle complex accommodating a nucleic acid therein, the number of repeating units in the cationic polymer chain block is preferably in a range of 10 to 200 and more preferably in a range of 20 to 100.

When a hydrophobic group is covalently bonded to the side chain or the terminal (terminal on the side opposite to the terminal covalently bonded to the uncharged hydrophilic polymer chain block in a direct or indirect manner) of the cationic polymer chain block, the obtained nucleic acid-encapsulating polymer micelle complex can be further stabilized. In a case where the side chain of the cationic polymer chain block includes a hydrophobic group, the manner of arrangement of the hydrophobic group in the cationic polymer chain block is not particularly limited, and examples thereof include a case where the hydrophobic group is arranged in the cationic polymer chain block in a random manner and a case where the hydrophobic group is arranged as a block (that is, a case where the uncharged hydrophilic polymer chain block; the cationic polymer chain block in which the hydrophobic group is covalently bonded to the side chain thereof; and the cationic polymer chain block formed of a repeating unit, not having a hydrophobic group forms a tri-block).

Examples of the hydrophobic group include a residue of a sterol derivative and a $C_{4-24}$ hydrocarbyl group. The sterol indicates a natural, semi-synthetic, or synthetic compound having a cyclopentanone hydrophenanthrene ring ($C_{17}H_{28}$) as a base. The natural sterol is not particularly limited, and examples thereof include cholesterol, cholestenol, dihydrocholesterol, and cholic acid. As the semi-synthetic or synthetic compound, a synthetic precursor of these natural products may be exemplified. The synthetic precursor includes a compound in which a part or all of a specific functional group and a hydroxy group is protected by a known hydroxyl-protecting group or a carboxyl group is protected by a carboxyl-protecting group in the technical field, if needed and if such a compound exists.

Furthermore, the sterol derivative means that a $C_{1-12}$ alkyl group or a halogen atom such as chlorine, bromine, or fluorine may be introduced to a cyclopentane hydrophenanthrene ring and the ring system may be saturated or partially unsaturated within a range that does not adversely affect the purpose of the present invention. As a residue of the sterol derivative, a group from which a hydrogen atom at the 3-position hydroxy group of cholesterol, cholestenol, or dihydroxy cholesterol is removed is preferable and a group from which a hydrogen atom at the 3-position hydroxy group of cholesterol is removed is more preferable. The $C_{4-24}$ hydrocarbyl group is a monovalent group generated by removing one hydrogen atom from hydrocarbon formed of 4 to 24 carbon atoms and a hydrogen atom. Specific examples thereof include a linear or branched $C_{4-24}$ alkyl group and preferably a linear or branched $C_{12-24}$ alkyl group; a linear or branched $C_{4-24}$ alkenyl group and preferably a linear or branched $C_{12-24}$ alkenyl group; a linear or branched $C_{4-24}$ alkynyl group and preferably a linear or branched $C_{12-24}$ alkynyl group; a $C_{4-24}$ cage compound and preferably a $C_{12-24}$ cage compound such as adamantyl; and an arylalkyl group in which aryl is phenyl or naphthyl and the alkyl group has 1 to 5 carbon atoms such as a benzyl group. As the hydrophobic group included in the side chain of the cationic polymer chain block in the block copolymer used in the present invention, a linear or branched $C_{4-20}$ alkyl group, a linear or branched $C_{4-20}$ alkenyl group or a benzyl group is preferable, a linear or branched $C_{12-20}$ alkyl group, a linear or branched $C_{12-20}$ alkenyl group, or a benzyl group is preferable, and a linear or branched $C_{12-20}$ alkyl group, a linear or branched $C_{12-20}$ alkenyl group, or a benzyl group is more preferable. In addition, the above-described alkenyl group and alkynyl group may include a plurality of unsaturated bonds.

Moreover, in the present specification, "$C_{x-y}$" means that the number of carbon atoms is in a range of x to y.

In the nucleic acid-encapsulating polymer micelle complex, it is preferable that block copolymers constituting the nucleic acid-encapsulating micelle complex be cross-linked in terms of stability of the polymer micelle complex. For example, when the side chain or the terminal (terminal on the side opposite to the terminal covalently bonded to the uncharged hydrophilic polymer chain block in a direct or indirect manner) of the cationic polymer chain block has a thiol group (—SH group) or a site bonded to a crosslinking agent, the obtained nucleic acid-encapsulating polymer micelle complex can be further stabilized. Thiol groups in the cationic polymer chain block can be cross-linked by a disulfide bond (SS bond).

As a site bonded to a crosslinking agent, an amino group (—$NH_2$ group), a thiol group, a hydroxyl group, or a carboxyl group is exemplified. Examples of the crosslinking group which can use any of these as a binding site include glutaraldehyde, succinaldehyde, paraformaldehyde, and phthalic dicarboxyaldehyde (phthalaldehyde) which include a plurality of aldehyde groups in a molecule; N-[α-maleimide acetoxy]succinimide ester, N-[3-maleimidepropyloxy] succinimide ester, N-[s-maleimidocaproyloxy]succinimide ester, N-[γ-maleimidobutyryloxy]succinimide ester, succinimidyl-4-[N-maleimidemethyl]cyclohexane-1-carboxy-[6-amidecaproate], m-maleimidobenzoyl-N-hydroxysuccinimide ester, succinimidyl-4-[N-maleimidemethyl] cyclohexane-1-carboxylate, succinimidyl-4-[p-maleimidophenyl]butyrate, and succinimidyl-6-[(β-maleimidopropionamido)hexanoate] which include a maleimide group and an active ester group in a molecule: N-5-azido-2-nitrobenzoyloxy succinimide and N-succinimidyl-6-[4'-azido-2'-nitrophenylamino]hexanoate which include an active ester and a nitrophenylazide group in a molecule; p-azidophenylglyoxal which has a phenyl azide group and a phenylglyoxalic group in a molecule; 1,4-bis-maleimide butane, bis-maleimide ethane, bis-maleimide hexane, 1,4-bis-maleimidyl-2,3-dihydrobutane, 1,8-bis-maleimide triethylene glycol, 1,11-bis-maleimide tetraethylene glycol, bis[2-(succinimidyloxycarbonyloxy)ethyl]sulfone, and tris-[2-maleimidoethyl]amine which include a plurality of maleimide groups in a molecule; bis[sulfosuccinimidyl] suberate, bis[2-(sulfosuccinimidoxycarbonyloxy)ethyl]sulfone, disulfosuccinimidyl tartrate, ethylene glycol bis[sulfosuccinimidylsuccinate], and tris-sulfosuccinimidylamino triacetate which include a plurality of sulfo active ester groups in a molecule; 1,5-difluoro-2,4-dinitrobenzene which includes a plurality of allyl halide groups in a molecule; dimethyl adipimidate, dimethyl pimelimidate, and dimethyl suberimidate which include a plurality of imide ester groups in a molecule; 1,4-di-[3'-(2'-pyridyldithio)propionamide]butane which includes a plurality of pyridyldithio groups in a molecule; disuccinimidyl glutarate, disuccinimidyl suberate, disuccinimidyl tartrate, and ethylene glycol bis[succinimidyl succinate] which include a plurality of active ester groups in a molecule; 1,6-hexane-bis-vinylsulfone which includes a plurality of vinyl sulfone groups in a molecule; succinimidyl-6-[3-(2-pyridyldithio)propionamide]hexanoate, 4-succinimidyloxycarbonyl-methyl-α-[2-pyridyldithio] toluene, and N-succinimidyl-3-[2-pyridyldithio]propionate which include a pyridyldithio group and an active ester group in a molecule; N-hydroxysuccinimidyl-4-azidosalicylic acid which includes a hydroxyphenylazide group and an active ester group in a molecule; N-[p-maleimidophenyl] isocyanate which includes a maleimide group and an isocyanate group in a molecule; N-[ε-maleimidocaproyloxy] sulfosuccinimide ester, N-[γ-maleimidobutyloxy] sulfosuccinimide ester, N-hydroxysulfosuccinimidyl-4- azidobenzoate, N-[κ-maleimidoundecanoyloxy]sulfosuccinimide ester, m-maleimidebenzoyl-N-hydroxysulfosuccinimide ester, sulfosuccinimidyl-4-[N-maleimidomethyl]cyclohexane-1-carboxylate, and sulfosuccinimidyl-4-[p-maleimidophenyl]butyrate which include a maleimide group and a sulfo active ester group in a molecule; sulfosuccinimidyl-6-[3'-(2-pyridyldithio)propionamide]hexanoate and sulfosuccinimidyl-6-[α-methyl-α-(2-pyridyldithio)toluamide]hexanoate which include a pyridyldithio group and a sulfo active ester group in a molecule; sulfosuccinimidyl[4-azidosalicylamido]hexanoate which includes a hydroxyphenyl azide group and a sulfo active ester group in a molecule; sulfosuccinimidyl-6-[4'-azide-2'-nitrophenylamino]hexanoate which includes a nitrophenylazide group and a sulfo active ester group in a molecule; and N-succinimidyl-[4-vinylsulfobnyl]benzoate which includes a vinyl sulfone group and an active ester group in a molecule. Among these, glutaraldehyde is particularly preferable.

<Block Copolymer>

The block copolymer used in the present invention is a copolymer in which the terminal of the uncharged hydrophilic polymer chain block is covalently bonded to the terminal of the cationic polymer chain block in a direct manner or indirect manner (that is, via a suitable linker).

As the block copolymer used in the present invention, a copolymer in which the uncharged hydrophilic polymer chain block is derived from polyethylene glycol and the cationic polymer chain block is derived from a polyamino acid or a derivative thereof is preferable and a copolymer in which the uncharged hydrophilic polymer chain block is derived from polyethylene glycol and the cationic polymer chain block is derived from a polyamino acid (also may be derived from a polyamino acid derivative) selected from the group consisting of polylysine, polyornithine, polyarginine, polyhomoarginine, polyhistidine, polyaspartic acid, and polyglutamic acid is more preferable.

As the block copolymer used in the present invention, specifically, one represented by the following Formula (I) or (II) can be exemplified. In addition, respective repeating units in the following Formulae (I) and (II) are shown in specified order for convenience of description, but the respective repeating units can be present in random order hydroxyl group, an oxybenzyl group, a —NH—$(CH_2)_8$—X group (here, a represents an integer of 1 to 5, X's each independently represents an amine compound residue containing one or more from among a primary amine, a secondary amine, a tertiary amine, and a quaternary ammonium salt or a compound residue which is not an amine), a thiol group, a hydrophobic group, or an initiator residue, $R^{5a}$, $R^{5b}$, $R^{5c}$, and $R^{5d}$ each independently represents a hydroxyl group, an oxybenzyl group, or a NH—$(CH_2)_a$—X group, at least two —NH—$(CH_2)_a$—X groups (here, X represents $(NH(CH_2)_2)_e$—$NH_2$ and e represents an integer of 1 to 5) are present among the total number of $R^{5a}$'s and $R^{5b}$'s and the total number of $R^{5c}$'s and $R^{5d}$'s, $R^{6a}$ and $R^{6b}$ each independently represents a hydrogen atom, a protecting group (here, a protecting group typically indicates a Z group, a Boc group, an acetyl group, or a trifluoroacetyl group used as a protecting group of an amino group), or $L^3$-SH ($L^3$ represents a linking group selected from the group consisting of a $C_{1-20}$ alkylene group, a $C_{1-6}$alkyl-phenyl group, a $C_{1-6}$alkyl-phenylene-$C_{1-6}$ alkyl group, a phenylene group, and a carbonyl-$C_{1-20}$ alkyl group), m represents an integer of 5 to 20000, n represents an integer of 2 to 5000, y represents an integer of 0 to 5000, z represents an integer of 1 to 5000, and y+z is set to be not greater than n. Furthermore, respective repeating units in Formulae (I) and (II) are shown in specified order for convenience of description, but the respective repeating units can be present in random order.]

Here, in the structural formulae of Formulae (I) and (II), a block in which the number of repeating units (polymerization degree) is "m" is a PEG block (uncharged hydrophilic polymer chain block) and a block in which the number of repeating units is a combination of the portion of "n-y-z," the portion of "y," and the portion of "z" is a cationic polymer chain block.

In Formulae (I) and (II), $R^{1a}$ and $R^{1b}$ each independently represents a hydrogen atom or an unsubstituted or substituted linear or branched $C_{1-12}$ alkyl group. Examples of the linear or branched $C_{1-12}$ alkyl group include a methyl group, an ethyl group, an n-propyl group, an iso-propyl group, an n-butyl group, a sec-butyl group, a tert-butyl group, an n-pentyl group, an n-hexyl group, a decyl group, and an undecyl group. Furthermore, examples of the substituent in a case of a substituted group include an acetalized formyl

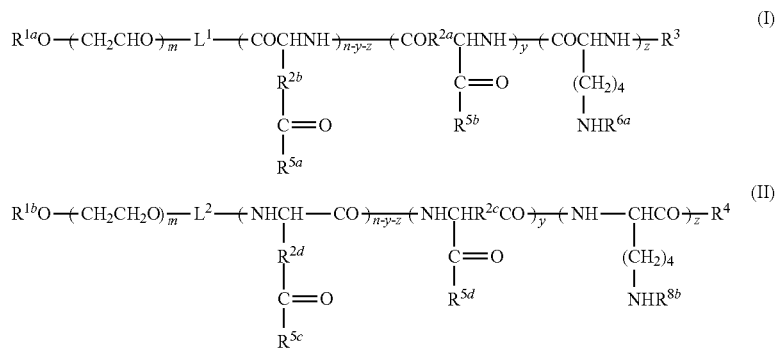

[In Formulae (I) and (II), $R^{1a}$ and $R^{1b}$ each independently represents a hydrogen atom or unsubstituted or substituted linear or branched $C_{1-12}$ alkyl group, $L^1$ and $L^2$ represent a linking group, $R^{2a}$ and $R^{2b}$ each independently represents a methylene group or an ethylene group, $R^3$ represents a hydrogen atom, a protecting group, a thiol group, a hydrophobic group, or a polymerizable group, $R^4$ represents a group, a cyano group, a formyl group, a carboxyl group, an amino group, a $C_{1-6}$alkoxycarbonyl group, a $C_{2-7}$ acylamide group, the same or different tri-$C_{1-6}$ alkylsiloxy group, a siloxy group, and a silylamino group. Here, the acetalization means formation of an acetal portion formed by a reaction of carbonyl of formyl with two molecules of alkanols having 1 to 6 carbon atoms or an alkylene diol which has 2 to 6 carbon atoms and may be branched and also means a method for protecting the carbonyl group. For example, in a case where the substituent is an acetalized formyl group, the group is hydrolyzed under a mild condition of acidity and can be converted to a formyl group (—CHO: or an aldehyde group), which is another substituent.

Moreover, in a case where groups including a substituent with high reactivity such as an amino group are used as $R^{1a}$ and $R^{1b}$ as needed, a bonding group having an active ester group and a maleimide group is further introduced according to the necessity through the substitution and then targeting molecules may be bonded thereto. Examples of the targeting molecules are as follows.

In Formulae (I) and (II), $L^1$ and $L^2$ represent a linking group. Specifically, it is preferable that $L^1$ represent —$(CH_2)_b$—NH— (here, b represents an integer of 0 to 5) and $L^2$ represents —$(CH_2)_c$—CO— (here, c represents an integer of 1 to 5). In addition, when b represents 0, "—$(CH_2)_b$—" represents a linking group.

In Formulae (I) and (II), $R^{2a}$, $R^{2b}$, $R^{2c}$, $R^{2d}$ each independently represents a methylene group or an ethylene group. When both of $R^{2a}$ and $R^{2b}$ represent a methylene group, the derivative corresponds to a poly(aspartic acid derivative). When both of $R^{2a}$ and $R^{2b}$ represent an ethylene group, the derivative corresponds to a poly(glutamic acid derivative). In addition, when both of $R^{2c}$ and $R^{2d}$ represent a methylene group, it corresponds to a poly(aspartic acid derivative). When both of $R^{2c}$ and $R^{2d}$ represent an ethylene group, it corresponds to a poly(glutamic acid derivative). In these formulae, when $R^{2a}$ and $R^{2b}$ ($R^{2b}$ and $R^{2a}$) represent both of a methylene group and an ethylene group and $R^{2c}$ and $R^{2d}$ ($R^{2d}$ and $R^{2c}$) represent both of a methylene group and an ethylene group, the repeating units of the aspartic acid derivative and the glutamic acid derivative are present after respectively forming blocks or can be present in a random manner.

In Formulae (I) and (II), $R^3$ represents a hydrogen atom, a protecting group, a thiol group, a hydrophobic group, or a polymerizable group. Specifically, it is preferable that $R^3$ represent an acetyl group, an acryloyl group, a methacryloyl group, a thiol group, or a hydrophobic group. Specifically, the hydrophobic group indicates residues of the above-described sterol derivative bonded to each other via a linking group $B^1$ [$B^1$ represents a single bond, —COO—, —CO—, —CO—$(CH_2)_h$—CO— (in this case, h represents an integer of 1 to 5), or the following Formula (III)] or a $C_{4-24}$ hydrocarbyl group. As the hydrophobic group in $R^3$, residues of a sterol derivative bonded to each other via the linking group $B^1$ are preferable, a group to which a group from which a hydrogen atom at the 3-position hydroxy group of cholesterol, cholestenol, or dihydroxy cholesterol is removed is bonded via the linking group $B^1$ is more preferable, a group to which a group from which a hydrogen atom at the 3-position hydroxy group of cholesterol is removed is bonded via the linking group $B^1$ is still more preferable.

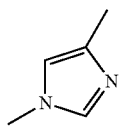

(III)

In Formulae (I) and (II), $R^4$ represents a hydroxyl group, an oxybenzyl group, a —NH—$(CH_2)_a$—X group, a thiol group, a hydrophobic group, or an initiator residue. Here, it is preferable that a represent an integer of 1 to 5 and X represents an amine compound residue containing one or two or more from among a primary amine, a secondary amine, a tertiary amine, and a quaternary ammonium salt or a compound residue which is not an amine. In some cases, it is preferable that $R^4$ represent —NH—$R^9$ (here, $R^9$ represents an unsubstituted or substituted linear or branched $C_{1-20}$ alkyl group). Specifically, the hydrophobic group is a residue of the above-described sterol derivative or a $C_{4-24}$ hydrocarbyl group. As the hydrophobic group in $R^4$, a residue of a sterol derivative is preferable, a group from which a hydrogen atom at the 3-position hydroxy group of cholesterol, cholestenol, or dihydroxy cholesterol is removed is preferable, and a group from which a hydrogen atom at the 3-position hydroxy group of cholesterol is removed is more preferable.

In Formulae (I) and (II), $R^{5a}$, $R^{5b}$, $R^{5c}$, and $R^{5d}$ each independently represents a hydroxyl group, an oxybenzyl group, or a —NH—$(CH_2)_a$—X group. Here, it is preferable that a represent an integer of 1 to 5 and X represents an amine compound residue containing one or two or more from among a primary amine, a secondary amine, a tertiary amine, and a quaternary ammonium salt or a compound residue which is not an amine.

Among the total number of $R^{5a}$'s and $R^{5b}$'s and the total number of $R^{5c}$'s and $R^{5d}$'s, it is preferable that at least two —NH—$(CH_2)_a$—X groups [here, X represents NH—$(CH_2)_e$—$NH_2$ (in this case, e represents an integer of 1 to 5)] be present, more preferable that —NH—$(CH_2)_a$—X groups be present in the proportion of 50% or greater of the total number of $R^{5a}$'s and $R^{5b}$'s and the total number of $R^{5c}$'s and $R^{5d}$'s, and still more preferable that —NH—$(CH_2)_a$—X groups be present in the proportion of 85% or greater of the total number of $R^{5a}$'s and $R^{5b}$'s and the total number of $R^{5c}$'s and $R^{5d}$'s. Furthermore, it is preferable that all or some of $R^{5a}$, $R^{5b}$, $R^{5c}$, and $R^{5d}$ represent —NH—$(CH_2)_a$—NH—$(CH_2)_e$—$NH_2$.

Moreover, in the above-described —NH—$(CH_2)_a$—X group represented by $R^4$, $R^{5a}$, $R^{5b}$, $R^{5c}$, or $R^{5d}$, it is particularly preferable that X be selected from the group consisting of groups represented by the following fifteen formulae.

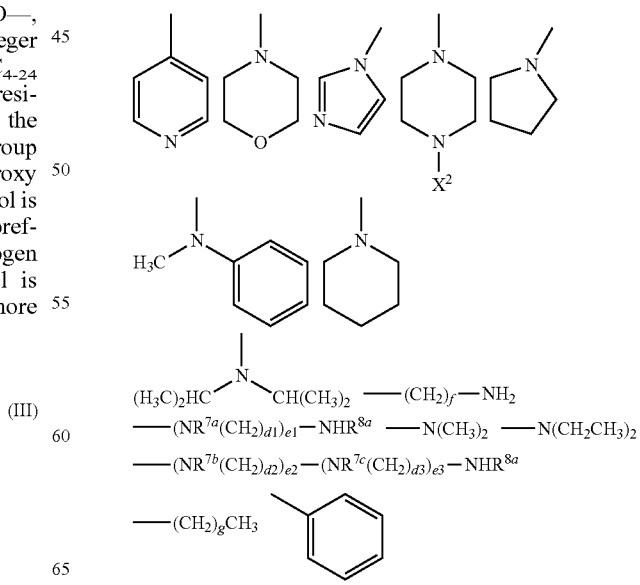

Here, in the respective formulae above, $X^2$ represents a hydrogen atom, a $C_{1-6}$ alkyl group, or an amino $C_{1-6}$alkyl group, $R^{7a}$, $R^{7b}$, and $R^{7c}$ each independently represents a hydrogen atom or a methyl group, d1, d2, and d3 each independently represents an integer of 1 to 5, e1, e2, and e3 each independently represents an integer of 1 to 5, f represents an integer of 0 to 15, g represents an integer of 0 to 15, and $R^{8a}$ and $R^{8b}$ each independently represents a hydrogen atom, a protecting group, $L^3$-SH ($L^3$ represents a linking group selected from the group consisting of a $C_{1-20}$ alkylene group, a $C_{1-6}$ alkyl-phenyl group, a $C_{1-6}$alkyl-phenylene-$C_{1-6}$ alkyl group, a phenylene group, and a carbonyl-$C_{1-20}$ alkyl group). Here, it is preferable that the protecting group be a group selected from the group consisting of a Z group, a Boc group, an acetyl group, and a trifluoroacetyl group typically used as protecting groups of amino groups. In addition, in a case where f and g represent 0, the respective formulae indicate a single bond.

In formulae (I) and (II), $R^{6a}$ and $R^{6b}$ each independently represents a hydrogen atom, a protecting group, or $L^3$-SH ($L^3$ represents a linking group selected from the group consisting of a $C_{1-20}$ alkylene group, a $C_{1-6}$ alkyl-phenyl group, a $C_{1-6}$ alkyl-phenylene-$C_{1-20}$ alkyl group, a phenylene group, and a carbonyl-$C_{1-20}$ alkyl group). Here, it is preferable that the protecting group be a group selected from the group consisting of a Z group, a Boc group, an acetyl group, and a trifluoroacetyl group typically used as protecting groups of amino groups.

In Formulae (I) and (II), m represents an integer of 5 to 20000. In addition, n represents an integer of 2 to 5000, y represents an integer of 0 to 5000, and z represents an integer of 1 to 5000. Here, (y+z), which is the total number of y and z, is set to be not greater than n.

A method for producing the block copolymers represented by Formulae (I) and (II) is not particularly limited, and examples thereof include a method for synthesizing a PEG block, which contains $R^{1a}O-$ or $R^{1b}O-$ and a PEG chain, in advance, sequentially polymerizing predetermined monomers on one terminal of the PEG block (terminal on the side opposite to $R^{1a}O-$ or $R^{1b}O-$), and then performing substitution or conversion such that the side chain contains a cationic group as needed and a method for synthesizing the above-described PEG block and a cationic polymer chain block (block in which the number of repeating units is a combination of a portion of "n-y-z," a portion of "y," and a portion of "z") in advance and then connecting these to each other. The methods and conditions of various reactions in the above-described production method can be suitably selected or set by referring to conventional methods. The PEG block can be prepared using methods for producing PEG blocks of block copolymers described in PCT International Publication Nos. WO96/32434, WO96/33233, and WO97/06202.

As a more specific example of the method for producing the block copolymers represented by Formulae (I) and (II), preferably, a method for polymerizing a N-carboxylic anhydride (NCA) of a protected amino acid such as β-benzyl-L-aspartate (BLA) or Ns-Z-L-lysine on a terminal of an amino group using a PEG block derivative having an amino group on the terminal to synthesize the block copolymer and performing substitution or conversion using diethylenetriamine (DET) such that the side chain of each block becomes a side chain having the above-described cationic group is exemplified.

In the present invention, specific examples of the block copolymers represented by Formulae (I) and (II) include a copolymer obtained by adding residues of a sterol derivative to PEG-poly[N—[N'-(2-aminoethyl)-2-aminoethyl)]aspart- amide] (PEG-PAsp (DET)), PEG-polylysine (PEG-PLys) described in Examples described below, or terminals of main chains of these cationic blocks in a direct manner or via a connecting group as needed and a copolymer obtained by adding a thiol group to side chains of these cationic blocks.

<Modification of Block Copolymer>

In order to use a polymer micelle complex as a gene carrier, it is preferable that the surface of the polymer micelle complex include molecules with high affinity for specific cells or tissues (targeting molecules) for the purpose of efficiently transporting a gene (DNA) to target tissues or target cells. For example, it is possible to form a nucleic acid-encapsulating polymer micelle complex in which targeting molecules are exposed to the surface thereof by adding the targeting molecules to the terminal, on the side opposite to the terminal covalently bonded to the cationic polymer chain block in a direct or indirect manner among two terminals of the uncharged hydrophilic polymer chain block, in a direct manner or via a linker. Examples of the targeting molecules include a ligand or an antibody (fragment thereof: F(ab')2 or F(ab)) against specific receptor protein, sugar, and nuclear localization signal molecules. The nucleic acid-encapsulating polymer micelle complex of the present invention is formed of exceptionally small particles in spite of encapsulation of DNA of 2000 or more base pairs in length. For this reason, when the surface layer includes nuclear localization molecules, gene transfer can be succeeded by passing through nuclear membrane pores even in non-dividing cells.

<Nucleic Acid-Encapsulating Polymer Micelle Complex>

A nucleic acid encapsulated in the nucleic acid-polymer micelle complex according to the present invention is two single-stranded DNAs having mutually complementary base sequences of 2000 or more bases in length or one single-stranded DNA of 2000 or more base pairs in length. In the two single-stranded DNAs having mutually complementary base sequences, double-stranded DNA formed by association of two DNAs each other typically has a double helix structure. Since the double helix structure is extremely rigid, in a case where a nucleic acid-encapsulating polymer micelle complex is formed according to a conventional method in which a polymer micelle complex encapsulating DNA is formed by simply mixing double-stranded DNA into a block copolymer for self-organization, small particles in the form close to a sphere could not be obtained unless the density of the uncharged hydrophilic polymer chain block in the shell portion is sufficiently lowered.

The nucleic acid-encapsulating polymer micelle complex according to the present invention encapsulates, as a core portion, two single-stranded DNAs having mutually complementary base sequences of 1000 or more bases in length (preferably 1500 or more bases in length and more preferably 2000 or more bases in length), double-stranded DNA of 1000 or more base pairs (preferably 1500 or more base pairs in length and more preferably 2000 or more base pairs in length) in length in which at least a part of the double helix structure is dissociated and a single-stranded structure is formed, or one single-stranded DNA of 1000 or more bases in length (preferably 1500 or more bases in length and more preferably 2000 or more bases in length). That is, in a case where the nucleic acid-encapsulating polymer micelle complex according to the present invention encapsulates double-stranded DNA such as pDNA, double-stranded DNA of 1000 or more base pairs in length (preferably 1500 or more base pairs in length and more preferably 2000 or more base pairs in length) is electrostatically bonded to a cationic polymer chain block in the block copolymer and encapsulated therein in a state in which at least a part and preferably all of the double helix structure is dissociated. Since single-stranded DNA acts as a flexible chain, condensation transition to a spherical shape becomes possible when the single-stranded DNA is electrostatically bonded to the block copolymer. That is, the surface area of the core portion (DNA) can be made extremely small and the density of the uncharged hydrophilic polymer chain block can be greatly increased in the shell portion.

The nucleic acid-encapsulating polymer micelle complex according to the present invention can be obtained by mixing double-stranded DNA into a block copolymer for self-organization in a state in which all or at least a part of the double helix structure of the double-stranded DNA is dissociated and forming a polymer micelle complex having DNA as a core. Since a spherical core can be obtained by condensing DNA as small as possible, it is preferable that double-stranded DNA encapsulated therein be mixed into a block copolymer in a state in which the double-stranded DNA is completely dissociated from each other to form two single-stranded DNAs and then is self-organized. In this manner, a nucleic acid-encapsulating polymer micelle complex having two single-stranded DNAs in the core or a nucleic acid-encapsulating polymer micelle complex having one single-stranded DNA in the core are formed. Furthermore, dissociation of the double helix structure of double-stranded DNA to the single-stranded structure can be appropriately performed using a conventional known denaturing method, for example, denaturation (thermal denaturation) through a heat treatment. The temperature of the heat treatment may be room temperature or higher, is preferably 60° C. or higher, more preferably 70° C. or higher, still more preferably 80° C. or higher, and particularly preferably 95° C. or higher. By performing the heat treatment at the above-described temperature or higher, the double helix structure of double-stranded DNA of 1000 or more base pairs in length can be preferably dissociated. The degree of dissociation of the double helix structure of the double-stranded DNA can be determined by examining a melting curve.

In the present invention, DNA encapsulated in a block copolymer may be in a state in which at least a part and preferably all of the double helix structure is dissociated at the time of mixing the DNA into the block copolymer or may be circular DNA. In the present invention, from a viewpoint of easily dissociating the double helix structure, linear DNA is preferable. When circular DNA is linearized by performing a restriction enzyme treatment or the like in advance, the double helix structure can be more easily dissociated.

The nucleic acid-encapsulating polymer micelle complex according to the present invention can be formed in the same manner as methods of forming a nucleic acid-encapsulating polymer micelle complexes disclosed in PTLs 1 to 3 except that double-stranded DNA encapsulated is mixed into a block copolymer in a state of being denatured (single-stranded). For example, examples of an aqueous medium which works as a reaction solvent that allows denatured DNA to be mixed into a block copolymer includes water (particularly ionized water) or a solution containing water and various inorganic or organic buffering agents. Furthermore, the aqueous medium may contain a water-miscible organic solvent such as acetonitrile, dimethylformamide, or ethanol within a range that does not adversely affect the reaction of forming the complex according to the present invention. The isolation and purification of the prepared nucleic acid-encapsulating polymer micelle complex can be recovered from the aqueous medium according to a conventional method. Examples of the typical method include an ultrafiltration method, a diafiltration method, and a dialysis method.

Moreover, in a case of a block copolymer including a thiol group in a cationic polymer chain block thereof, cationic polymer chain blocks can be cross-linked using an SS bond via the thiol group by forming a polymer micelle complex encapsulating DNA and then placing an aqueous medium containing the polymer micelle complex under an oxidation condition. Typically, the oxidation condition may be prepared by leaving the ambient environment as it is or setting a condition of air oxidation. The degree of crosslinking is not particularly limited, but it is preferable that an SH group be introduced to the cationic polymer chain block forming a polymer micelle complex in the proportion of 5% to 20% and preferably 8% to 15% and all thiol groups be oxidized.

In the nucleic acid-encapsulating polymer micelle complex according to the present invention, the average particle diameter in an aqueous medium measured by a dynamic light scattering method is preferably 100 nm or less, more preferably 80 nm or less, and still more preferably 70 nm or less. Since the nucleic acid-encapsulating polymer micelle complex according to the present invention is extremely small, the complex can be efficiently incorporated in a target cell or tissue. Furthermore, the particle diameter of the nucleic acid-encapsulating polymer micelle complex in an aqueous medium can be measured using a dynamic light scattering type particle diameter and particle size distribution measuring device for which a non-contact backscattering optical system (NIBS) is used. As the device, a Zetasizer Nano ZS (trade name, manufactured by Malvern Instruments Ltd.) is exemplified. In addition, the average particle diameter of the nucleic acid-encapsulating polymer micelle complex in an aqueous medium indicates the zeta average hydrodynamic particle diameter in the aqueous solution measured by a dynamic light scattering method.

The core portion (DNA) of the nucleic acid-encapsulating polymer micelle complex according to the present invention can be observed by a transmission electron microscope (TEM). The core portion of the nucleic acid-encapsulating polymer micelle complex according to the present invention is not rod-like but spherical. When the nucleic acid-encapsulating polymer micelle complex according to the present invention is practically observed by a TEM, a circular core portion, which is not rod-like, is observed. In the present invention and the specification of the present application, the term "spherical" shape includes not only an authentic sphere but also an ellipsoid close to a sphere (for example, an ellipsoid in which the ratio of the longest diameter among three diameters to one diameter among remaining diameters is in a range of 2:1 to 1:1). When the core portion of the nucleic acid-encapsulating polymer micelle complex according to the present invention is spherical, the average density of the block copolymer per surface area of the core portion can be increased compared to a case of the nucleic acid-encapsulating polymer micelle complex having a rod-like core portion. When the average density of the block copolymer per surface area of the core portion is higher, the nucleic acid-encapsulating micelle complex according to the present invention is unlikely to be affected by polyanions present intracellularly and extracellularly in abundance in a living body, and in-vivo stability can be improved.

In regard to the size of the nucleic acid-encapsulating polymer micelle complex according to the present invention, the average particle diameter of the core portion is preferably 50 nm or less, more preferably 40 nm or less, still more preferably 30 nm or less, and even still more preferably 25 nm or less. Furthermore, in the present invention and the specification of the present application, the "core portion of the nucleic acid-encapsulating polymer micelle complex" indicates an imaged portion in a case where the nucleic acid-encapsulating polymer micelle complex is imaged by a TEM and the "particle diameter of the core portion" indicates a spherical radius (that is, a circular radius of the core portion imaged in a TEM image). The particle diameter of the core portion of the nucleic acid-encapsulating polymer micelle complex can be acquired from the TEM image as shown in Reference Example (6) described below.

In the nucleic acid-encapsulating polymer micelle complex according to the present invention, the average density of the block copolymer per surface area of the core portion is preferably 0.01 chain/nm$^2$ or greater, more preferably 0.03 chain/nm$^2$ or greater, and still more preferably 0.05 chain/nm$^2$ or greater. Since the block copolymer density of the nucleic acid-encapsulating polymer micelle complex according to the present invention can be sufficiently increased, a complex with excellent retention in blood can be obtained in a case of systemic administration.

Moreover, the average density of the block copolymer per surface area of the core portion of the nucleic acid-encapsulating polymer micelle complex can be calculated according to the following method. First, the nucleic acid-encapsulating polymer micelle complex according to the present invention is obtained using a fluorescence-labeled copolymer. Next, the complex is centrifugally removed from a reaction solvent and block copolymers which are not involved in formation of the complex and are contained in a supernatant is quantified using fluorescence intensity as an index. The number of molecules of the block copolymer bonded to the complex is calculated using a difference from the total number of block copolymers used at the time of preparing the complex and the average number of molecules (unit: chain) of the block copolymer forming one molecule of the nucleic acid-encapsulating polymer micelle complex is calculated by dividing the calculated number of molecules by the number of molecules of double-stranded DNA used for the reaction. Further, the average surface area (nm$^2$) of the core portion per one molecule of the nucleic acid-encapsulating polymer micelle complex is calculated by imaging a TEM image of the obtained nucleic acid-encapsulating polymer micelle complex, acquiring the lengths of the radii of circles of respective core portions of a plurality of nucleic acid-encapsulating polymer micelle complexes in the obtained TEM image, and calculating the surface areas of the core portions of the respective nucleic acid-encapsulating polymer micelle complexes using a rotation sphere that uses the radius on the TEM image as the rotation axis. Finally, the average density (chain/nm$^2$) of the block copolymer per surface area of the core portion of the nucleic acid-encapsulating polymer micelle complex is acquired by dividing the average number of molecules of the block copolymer forming one molecule of the nucleic acid-encapsulating polymer micelle complex by the average surface area of the core portion per one molecule of the nucleic acid-encapsulating polymer micelle complex.

EXAMPLES

Hereinafter, the present invention will be described in more detail with reference to Examples and the like, but the present invention is not limited thereto. In addition, all animal experiments described below were performed in accordance with the guidelines related to management and use of experimental animals as stipulated by the National University Corporation, the University of Tokyo.

Reference Example 1

In a polymer micelle complex encapsulating double-stranded DNA (pDNA) having a double helix structure formed of a block copolymer which has a PEG block and a PLys block, the relationship between the polymerization degree of the PLys block and the shape of the polymer micelle complex was examined.

(1) PEG-PLys

A PEG block-poly(ε-trifluoroacetyl-L-lysine) block (PEG-PLys (TFA)) was prepared by ring-opening polymerization of a N-carboxylic anhydride (NCA) of N$_\varepsilon$-trifluoroacetyl-L-lysine using α-methoxy-ω-amino PEG (PEG, Mw=12 kDa, $M_w/M_n$=1.05), as an initiator, obtained according to a method disclosed by one of the present inventors (Kataoka et al., Macromoleculars, 1996, vol. 29, p. 8556 and 8557). At this time, three kinds of PEG-PLys' (TFA) with different polymerization degrees from each other were prepared by adjusting the ratio of the initiator to NCA, which is a monomer. In this manner, the trifluoroacetyl groups (TFA group) of the obtained three kinds of PEG-PLys' (TFA) were deprotected using sodium hydroxide, thereby obtaining three kinds of PEG-PLys' having different polymerization degrees from each other ("n1" in the following formula).

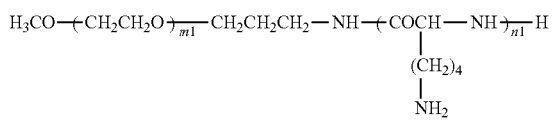

The polymerization degrees of PLys blocks of respective PEG-PLys' were acquired using the ratio of the total amount of protons of methylene of a PEG chain (—CH$_2$CH$_2$O—) obtained by $^1$H-NMR measurement to the total amount of protons of methylene of a lysine repeating unit [—(CH$_2$)$_3$CH$_2$NH$_3$], and the values were respectively 19, 39, 70. In addition, as a result of gel permeation chromatography (GPC) (using a high-speed GPC device HLC-8220GPC manufactured by TOSOH CORPORATION), the dispersity ($M_w/M_n$) of all three PEG-PLys was less than 1.1.

(2) Fluorescence-Labeled PEG-PLys

The PEG-PLys was fluorescence-labeled in advance in order to confirm that the PEG-PLys was bonded to DNA. Specifically, with respect to the PEG-PLys obtained in (1) described above, Alexa Fluor (registered trademark) 680 carboxylic acid succinimidyl ester (manufactured by Molecular Probes Inc.) was reacted and bonded according to for manufacturer's instructions. An unreacted fluorescent substance was removed using a PD-10 desalting column (manufactured by GE Healthcare Life Sciences Inc.). The fact that the PEG-PLys was practically fluorescence-labeled was confirmed by GPC including a UV detector, an IR detector, and a fluorescent detector. According to a calculation of the fluorescence labeling efficiency, one molecule of a fluorescent substance per 40 lysine repeating units was bonded in almost all PEG-PLys'.

(3) Nucleic Acid Used

In order to form a nucleic acid-encapsulating micelle complex for measuring an average density σ of the PEG per surface area of the core portion, commercially available plasmid pBR322 (4361bp, manufactured by Takara Bio Inc.) was used. In order to form a nucleic acid-encapsulating micelle complex for examining retention in blood, plasmid pCAG-Luc2 (6.4 kbp) labeled by a fluorescent substance Cy (registered trademark) 5 was used. The fluorescence-labeling of the pCAG-Luc2 was performed using Label IT (registered trademark) Tracker Nucleic Acid Localization Kit (manufactured by Mirus Bio LLC). In addition, the pCAG-Luc2 was obtained by incorporating the genes coding Luc2 which is cut from plasmid pGL4 (manufactured by Promega Corporation) in plasmid pCAGGS (provided from RIKEN Gene Bank).

(4) Formation of Nucleic Acid-encapsulating Polymer Micelle Complex

A polymer micelle complex of the PEG-PLys encapsulating pDNA was formed by rapidly mixing a DNA solution into a PEG-PLys solution such that an N/P ratio became 2. Here, the N/P ratio means [molar concentration of amine group in PLys block]/[molar concentration of phosphate acid group in pDNA]. A 10 mM HEPES buffer (pH 7.3) was used as the reaction solvent. The pDNA concentration of the reaction solution was set as 33.3 ng/μL in a case of forming a nucleic acid-encapsulating polymer micelle complex for measuring the average density (a) of PEG and set as 100 ng/μ in a case of forming a nucleic acid-encapsulating polymer micelle complex for measuring retention in blood.

(5) Determination of PEG-PLys Forming Nucleic Acid-encapsulating Polymer Micelle Complex In regard to a polymer micelle complex which was formed using fluorescence-labeling PEG-PLys, an ultracentrifugation treatment was performed by putting a reaction solution after the polymer micelle complex was formed in a polycarbonate tube (product No: 343776, manufactured by Beckman Coulter Inc.) with a thick wall in order to separate fluorescence-labeled PEG-PLys bonded to pDNA from free fluorescence-labeled PEG-PLys which was not bonded to pDNA. The ultracentrifugation treatment was performed at 50000×g for 3 hours using an ultracentrifuge Optima TLX (manufactured by Beckman Coulter Inc.) equipped with TLA-120.1 rotor (manufactured by Beckman Coulter Inc.). Under the above-described conditions, the polymer micelle complex was completely precipitated while the free PEG-PLys remained in the supernatant, and this was confirmed by an ultracentrifuge XL-I (manufactured by Beckman Coulter Inc.) for Beckman analysis. The fluorescence intensity at 702 nm of the supernatant was measured and then the concentration of the fluorescence-labeled PEG-PLys in the supernatant was calculated using a calibration curve prepared based on the results of a standard product of the free fluorescence-labeled PEG-PLys. In addition, "702 nm" is the maximum fluorescence wavelength of a fluorescent substance Alexa Fluor (registered trademark) 680.

An amount obtained by subtracting the amount of the fluorescence-labeled PEG-PLys in the supernatant from the amount of the fluorescence-labeled PEG-PLys originally added to a reaction solution for forming a polymer micelle complex was set the total amount (mole) of the fluorescence-labeled PEG-PLys' contained in all the formed polymer micelle complexes and this total amount was subtracted by the amount (mole) of DNA originally added to the reaction solution, thereby calculating the average number of molecules (that is, the average number of molecules of the fluorescence-labeled PEG-PLys contained in one molecule of polymer micelle complex, unit: chain) of the fluorescence-labeled PEG-PLys bonded to one molecule of pDNA.

As a result, in regard to the average number of molecules of fluorescence-labeled PEG-PLys' contained in one molecule of polymer micelle complex, the value was 436±31.2 chains in a case of a polymer micelle complex containing fluorescence-labeled PEG-PLys' in which the polymerization degree of a PLys block was 19, 258±10.4 chains in a case of a polymer micelle complex containing fluorescence-labeled PEG-PLys' in which the polymerization degree of a PLys block was 39, and the value was 168±2.5 chains in a case of a polymer micelle complex containing fluorescence-labeled PEG-PLys' in which the polymerization degree of a PLys block was 70. In other words, it is understood there is a tendency that the average number of molecules of the fluorescence-labeled PEG-PLys' contained in one molecule of polymer micelle complex becomes smaller as the polymerization degree of a cationic polymer chain block of a block copolymer constituting a nucleic acid-encapsulating polymer micelle complex becomes greater.

(6) TEM Observation

A TEM image of the polymer micelle complex formed using the PEG-PLys was imaged. DNA and PLys blocks constituting the polymer micelle complex were shown in the TEM image and PEG was not able to be observed. In the polymer micelle complex, DNA forms the core portion. That is, the shape of the core portion of the polymer micelle complex can be confirmed from the TEM image.

The TEM observation and acquisition of an image were carried out under an acceleration voltage condition of 75 kV using an electron microscope H-7000 (manufactured by Hitachi High-Technologies Corporation). Measurement samples were prepared by adding a 2 mass/vol % uranyl acetate solution to a polymer micelle complex solution in an amount equal to that of the solution. A carbon film-coated copper grid having 400 openings (manufactured by Nissin EM Co., Ltd.) which was glow-discharged in advance using an ion coater (device name: Eiko IB-3, manufactured by Eiko Engineering Co., Ltd.) was immersed in the each measurement sample for 30 seconds and dried on filter paper, and the resultant was TEM observed. The core portion of the polymer micelle complex in the TEM image was rod-like and the length ($L_n$) of a long axis and the length ($2r_n$) of a short axis were observed using image processing software ImageJ.

FIG. 1 shows a TEM image (left in the figure) of a polymer micelle complex formed using PEG-PLys and distribution (right in the figure) of long axes ($L_n$) (lengths of rod-like particles) of the polymer micelle complex calculated from the image. In FIG. 1, the "PLys 19" shows the result of a polymer micelle complex containing fluorescence-labeled PEG-PLys in which the polymerization degree of a PLys block is 19, the "PLys 39" shows the result of a polymer micelle complex containing fluorescence-labeled PEG-PLys in which the polymerization degree of a PLys block is 39, and the "PLys 70" shows the result of a polymer micelle complex containing fluorescence-labeled PEG-PLys in which the polymerization degree of a PLys block is 70. As a result, it was understood that the size of the core portion of a complex micelle complex becomes smaller and the shape thereof becomes closer to a sphere from a rod shape as the polymerization degree of the PLys block becomes greater.

(7) Calculation of Surface Area of Core Portion and Calculation of Average Density σ of PEG Surface areas [$A_n$] of core portions of the respective polymer micelle complexes were acquired as follows, as a cylinder in which a long axis [$L_n$] in the TEM image was set as a rotation axis and a length [$r_n$] which was half of the short axis was set as the radius. A plurality of core portions in the TEM image was measured and the average thereof was calculated.

Surface area of core portion: $[A_n]=(L_n \times 2\pi r_n)+2\times(\pi \times r_n^2)$ Subsequently, the average density σ (chain/nm²) of a block copolymer per surface area of a core portion of a nucleic acid-encapsulating polymer micelle complex was acquired by subtracting the average number (chain) of molecules of fluorescence-labeled PEG-PLys' contained in one molecule of polymer micelle complex acquired in (5) described above by the average surface area of the core portion of the polymer micelle complex.

As a result, in regard to the average density σ of a block copolymer per surface area of a core portion of a nucleic acid-encapsulating polymer micelle complex, the value was 0.075 chain/nm² in a case of a polymer micelle complex containing fluorescence-labeled PEG-PLys's in which the polymerization degree of a PLys block was 19, the value was 0.051 chain/nm² in a case of a polymer micelle complex containing fluorescence-labeled PEG-PLys's in which the polymerization degree of a PLys block was 39, and the value was 0.038 chain/nm² in a case of a polymer micelle complex containing fluorescence-labeled PEG-PLys' in which the polymerization degree of a PLys block was 70. In other words, it is understood there is a tendency that the average density σ of a block copolymer per surface area of a core portion becomes smaller as the polymerization degree of a cationic polymer chain block of a block copolymer constituting a nucleic acid-encapsulating polymer micelle complex becomes greater.

(8) Evaluation of Retention in Blood

A polymer micelle complex formed using fluorescence-labeled DNA was administered to a mouse and the retention time of the complex in blood was observed over time using a biological real-time confocal scanning microscope. All images and videos were acquired by a confocal laser scanning microscope system A1R (manufactured by Nikon Corporation) equipped with an upright microscope ECLIPSE FN1 (manufactured by Nikon Corporation) (objective lens: 20 times, diode laser: 640 nm, emission band pass filter: 700/75 nm).

Specifically, first, 8-week-old female BALB/c mice (obtained from Charles River Laboratories Inc.) were anesthetized by 2.0% to 3.0% of isoflurane (manufactured by Abbott Japan Co., Ltd.) using an isoflurane anesthesia machine (model: 400, manufactured by Univentor Ltd.) for small animals. A catheter connected to a non-toxic medical polyethylene tube (manufactured by Natsume Seisakusho Co., Ltd.) was inserted to side tail veins of these mice together with a 30-gauge needle (manufactured by Becton Dickson and Company). The anesthetized mice were placed on a temperature control pad (product name: THERMOPLATE (registered trademark), manufactured by Tokai Hit Co., Ltd.) and sedation was maintained during the measurement. Next, a polymer micelle complex (injection amount: 200 µL, DNA concentration: 100 ng/µL) encapsulating fluorescence-labeled pDNA was injected to mice from the tail vein after 10 seconds from the start of recording of video. The skin of the earlobe was fixed below a cover clip together with one drop of immersion oil and then observed without surgical treatment. The data was acquired as snapshots in a video mode every five minutes. The experiments of each polymer micelle complex were performed four times using separate mice.

The video data was analyzed by selecting regions of interest from skin tissues in blood vessels or skin tissues other than blood vessels. First, the background fluorescence intensity was determined based on the video acquired during the 10 seconds (before the polymer micelle complex was injected) from the start of recording of video and the average fluorescence intensity per pixel at each time point was determined using image integration software NIS-Elements C (manufactured by Nikon Corporation). In order to obtain background-corrected intensity at each time point, the background value was subtracted from the average intensity per pixel measured after the polymer micelle complex was injected. The circulation of the polymer micelle complex in the body was monitored using fluorescence intensity from vessels in which fluorescence from the tissue background was subtracted.

Figure 2:
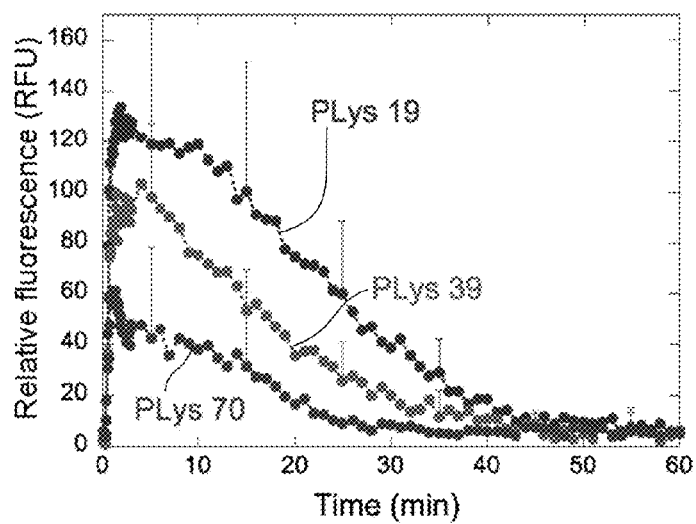
FIG. 2 is a diagram showing results of measurement of a change in fluorescence intensity of an ear vein of a mouse to which respective polymer micelle complexes are systemically administered over time in Reference Example 1.

FIG. 2 shows results of measurement of a change in fluorescence intensity of an ear vein of a mouse over time. From the start of the experiment to when 40 minutes passed, the fluorescence intensity of blood vessels was the highest in a case of a mouse to which a polymer micelle complex containing PEG-PLys in which the polymerization degree of a PLys block was 19 was administered ("PLys 19" in the figure) and the fluorescence intensity of blood vessels was the lowest in a case of a mouse to which a polymer micelle complex containing PEG-PLys in which the polymerization degree of a PLys block was 70 was administered ("PLys 70" in the figure). In other words, it was understood that retention in blood was excellent when the polymerization degree of a cationic polymer chain block of a block copolymer constituting a nucleic acid-encapsulating micelle complex is small, that is, when the density of a block copolymer constituting a nucleic acid-encapsulating micelle copolymer was high.

Example 1

Between a nucleic acid-encapsulating polymer micelle complex produced using a conventional method that allows a complex to encapsulate pDNA as it is and a nucleic acid-encapsulating polymer micelle complex produced using a method that allows pDNA to be bonded to a block copolymer in a state in which the double helix structure of pDNA was dissociated, the shapes, size, and density of the block copolymers were compared to each other.

(1) PEG-PAsp (DET)-Chole

A PEG block-poly(β-benzyl-L-aspartate) block (PEG-PBLA) was prepared by ring-opening polymerization of an NCA of β-benzyl-L-aspartate (BLA) using α-methoxy-ω-amino PEG (PEG, Mw=12 kDa, $M_w/M_n$=1.05) as an initiator. At this time, three kinds of PEG-PBLAs with different polymerization degrees from each other were prepared by adjusting the ratio of the initiator to NCA, which is a monomer.

A cholesterol derivative including a carboxyl group, activated by reacting with succinic anhydride after substitution of a 3-hydroxyl group of cholesterol with a primary amino group, was allowed to react on an amino group of the terminal of the obtained PEG-PBLA overnight in N,N-dimethylformamide in the presence of dicyclohexylcarbodiimide of 10 times equivalent and 4-dimethylaminopyridine of 2 times equivalent. The obtained block copolymer was added dropwise to and re-precipitated in a mixed solvent (2:1 (volume ratio)) of cold diethyl ether and isopropanol and this process was repeated three times, and then the resultant was freeze-dried from benzene, thereby obtaining purified powder of PEG-PBLA-Chole.

PEG-PAsp (DET)-Chole was obtained by introducing diethylenetriamine to the side chain of PBLA using the obtained PEG-PBLA-Chole by an ester-amide exchange reaction.

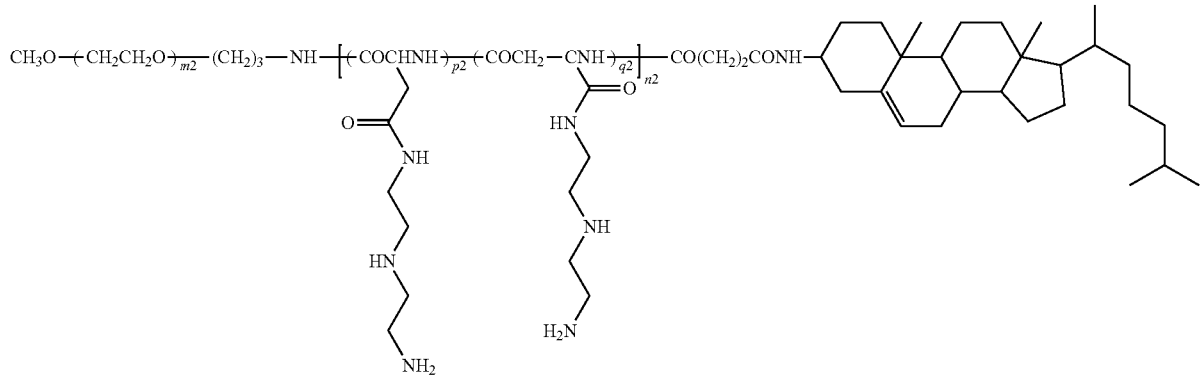

(2) Fluorescence-labeled PEG-PAsp (DET)-Chole

The PEG-PAsp (DET)-Chole was fluorescence-labeled in advance using Alexa Fluor (registered trademark) 680 carboxylic acid succinimidyl ester (manufactured by Molecular Probes Inc.) in the same manner as in (1) of Reference Example 1 in order to confirm that the PEG-PAsp (DET)-Chole was bonded to DNA. The fact that the PEG-PAsp (DET)-Chole was practically fluorescence-labeled was confirmed by GPC including a UV detector, an IR detector, and a fluorescent detector. When the fluorescence labeling efficiency was calculated, 0.3 molecules to 0.5 molecules of a fluorescent substance was bonded to one PAsp (DET) block in almost all PEG-PAsp (DET)-Choles.

(3) Formation of Nucleic Acid-Encapsulating Polymer Micelle Complex Encapsulating pDNA as it is A polymer micelle complex of the PEG-PAsp (DET)-Chole encapsulating pDNA (hereinafter, "PM-1" (PM: Polyplex Micelle)) was formed by rapidly mixing a plasmid pBR322 solution used in Reference Example 1 into a PEG-PAsp (DET)-Chole solution such that an N/P ratio became 4. A 10 mM HEPES buffer (pH 7.3) was used as the reaction solvent. The pDNA concentration of the reaction solution was set as 33.3 ng/μL.

(4) Formation of Nucleic Acid-encapsulating Polymer Micelle Complex Encapsulating pDNA after Denaturation A restriction enzyme was added to a plasmid pCAG-Luc (6.4 kbp) solution, the solution was subjected to a restriction enzyme treatment, and then pCAG-Luc was formed to have a linear shape through one site digestion. A DNA solution containing this linear DNA was subjected to a heat treatment at 95° C. for 10 minutes and the linear pCAG-Luc was denatured to be a single-strand. Next, by rapidly mixing the PEG-PAsp (DET)-Chole solution into the DNA solution in the denaturation state such that the N/P ratio became 4, a polymer micelle complex of PEG-PAsp (DET)-Chole (hereinafter, "MCPM-1" (MCPM: Melt Crumpled Polyplex Micelle)) encapsulating two linear single-stranded DNAs derived from one molecule of pCAG-Luc was formed. A 10 mM HEPES buffer (pH 7.3) was used as a solvent. The pDNA concentration of the reaction solution was set as 33.3 ng/μL. Here, the pCAG-Luc was obtained by cutting out genes coding Luc from plasmid pGL3 (manufactured by Promega Corporation) and incorporating the genes in plasmid pCAGGS (provided from RIKEN Gene Bank).

(5) Determination of PEG-PAsp (DET)-Chole Forming Nucleic Acid-encapsulating Polymer Micelle Complex In regard to a polymer micelle complex which was formed using fluorescence-labeling PEG-PAsp (DET)-Chole between the polymer micelle complex obtained in (3) and (4) described above, a reaction solution after the polymer micelle complex was subjected to an ultracentrifugation treatment in the same manner as in (5) of Reference Example 1 in order to measure the amount of fluorescence-labeling PEG-PAsp (DET)-Chole bonded to DNA, and the average number of molecules (that is, the average number of molecules of the fluorescence-labeled PEG-PAsp (DET)-Chole contained in one molecule of polymer micelle complex, unit: chain) of fluorescence-labeling PEG-PAsp (DET)-Chole bonded to one molecule of pDNA was calculated based on the fluorescence intensity at 702 nm of the supernatant. The calculation results are listed in the section "number of bonded PEGs (chain)" of Table 1.

(6) TEM Observation

Figure 3:
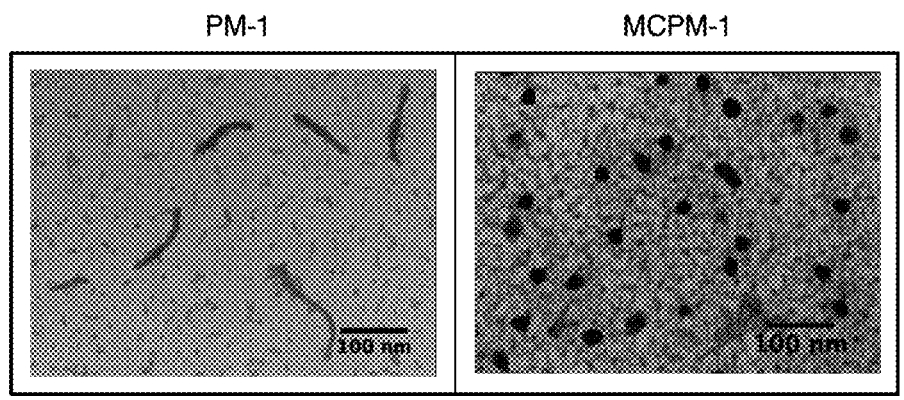
FIG. 3 shows TEM images of polymer micelle complexes (left: PM-1, right: MCPM-1) of Example 1 formed using fluorescence-labeled PEG-PAsp (DET)-Chole.
Figure 4:
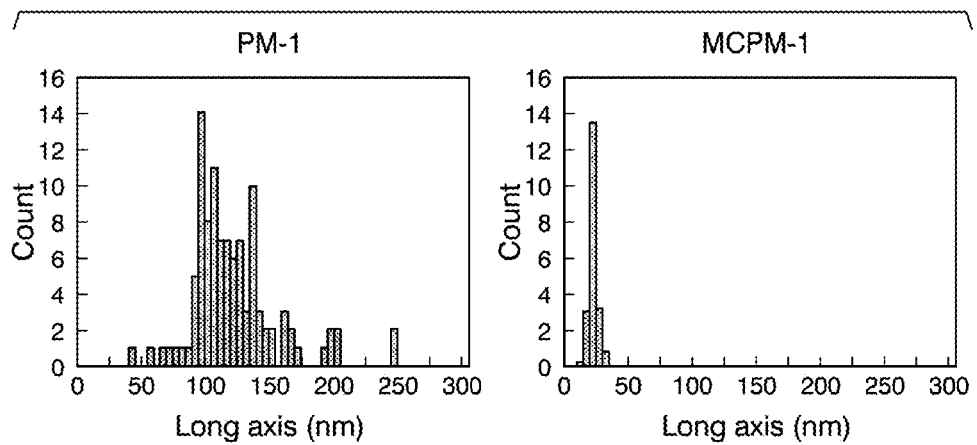
FIG. 4 shows diagrams (left: PM-1, right: MCPM-1) of distribution of long axis lengths of polymer micelle complexes of Example 1 calculated from the TEM images.

In regard to the polymer micelle complex formed using PEG-PAsp (DET)-Chole which is not fluorescence labeled, between the polymer micelle complexes obtained in (3) and (4) described above, a TEM image was taken in the same manner as in (6) of Reference Example 1. Then, the length of a long axis $[(L_n)]$ and the length of a short axis $[(2r_n)]$ of the core portion of the polymer micelle complex in the TEM image were observed. At this time, in a case where the shape of the core portion is a circle, the length of the long axis $[(L_n)]$ becomes a diameter and equivalent to the length of a short axis $[(2r_n)]$. FIG. 3 shows TEM images of both polymer micelle complexes and FIG. 4 shows distribution of long axes of polymer micelle complexes calculated from the TEM images. In the TEM image, the core portion of the polymer micelle complex in PM-1 was rod-like similar to Reference Example 1, but the core portion of the polymer micelle complex in MCPM-1 was spherical (average radius: 23.1±3.8 nm).

(7) Calculation of Surface Area of Core Portion and Calculation of Average Density σ of PEG Surface areas $[A_n]$ of core portions of a plurality of PM-1s in the TEM image were calculated in the same manner as in (7) of Reference Example 1 and the average thereof was calculated.

Using a sphere in which a length $[r_n]$ which was half of the long axis $[L_n]$ in the TEM image was set as the radius, surface areas $[A_n]$ of core portions of MCPM-1s were acquired as follows. A plurality of core portions in the TEM image were measured and the average thereof was calculated.

Surface area of core portion: $[A_n]=4\pi r_n^2$

Subsequently, the average density σ (chain/nm²) of a block copolymer per surface area of a core portion of a nucleic acid-encapsulating polymer micelle complex was acquired by subtracting the average number (chain) of molecules of fluorescence-labeled PEG-PAsp (DET)-Choles contained in one molecule of polymer micelle complex acquired in (5) described above by the average surface area of the core portion of the polymer micelle complex. The calculation results of the average value of the surface areas of core portions and the average density σ of block copolymers per surface areas of core portions were respectively listed as "surface area (nm²) of core portion" and "PEG density σ (chain/nm²)" in Table 1.

TABLE 1

|  | PM-1 | MCPM-1 |
| --- | --- | --- |
| Surface area of core portion (nm²) | 4927 | 1414 |
| Number of bonded PEGs (chain) | 474 | 465 |
| PEG density σ (chain/nm²) | 0.096 | 0.328 |

As a result, although PM-1 and MCPM-1 encapsulate the same size of DNA, PM-1 produced according to a conventional method had a shape of a rod, in which the long axis had a length of 100 nm to 150 nm, and had a PEG density of less than 0.1 chain/nm². Meanwhile, in MCPM-1 that forms a polymer micelle complex by dissociating the double helix structure of DNA, the core portion had a shape of a sphere with a radius of approximately 23 nm, which was extremely small and the PEG density was 0.3 chain/nm² or greater, which was significantly high. In other words, it is understood that a smaller nucleic acid-encapsulating polymer micelle complex in which the average density of a block copolymer per surface area of a core portion is high and which has a shape of a sphere can be formed by dissociating the double helix structure of DNA and forming a polymer micelle complex.

Example 2

Using plasmid pCAG-AcGFP (6.5 kbp, provided from RIKEN Gene Bank) containing genes coding green fluorescent protein GFP in the downstream of a CAG promoter, GFP gene-encapsulating polymer micelle complexes were produced according to a conventional method that allows pDNA to be incorporated as it is and a method that allows pDNA to be bonded to a block copolymer in a state in which the double helix structure of pDNA is dissociated. Further, the complexes were systemically administered to model mice having pancreatic cancer and GFP expression in pancreatic cancer tissues was examined. In addition, the pCAG-AcGFP was obtained by incorporating genes coding GFP in the plasmid pCAGGS (provided from RIKEN Gene Bank).

(1) Formation of Nucleic Acid-Encapsulating Polymer Micelle Complex Encapsulating pGFP as it is A polymer micelle complex of the PEG-PAsp (DET)-Chole encapsulating pDNA (hereinafter, "PM-2-GFP") was formed by rapidly mixing a plasmid pGFP solution into the PEG-PAsp (DET)-Chole solution produced in Example 1 such that the N/P ratio became 4. A 10 mM HEPES buffer (pH 7.3) was used as the reaction solvent. The plasmid concentration of the reaction solution was set as 100 g/μL.

(2) Formation of Nucleic Acid-encapsulating Polymer Micelle Complex Encapsulating pGFP after Denaturation A restriction enzyme was added to a plasmid pGFP solution, the solution was subjected to a restriction enzyme treatment, and then pGFP was formed to have a linear shape through one site digestion. A DNA solution containing this linear DNA was subjected to a heat treatment at 95° C. for 10 minutes and the linear pGFP was denatured to be single-stranded. Next, by rapidly mixing the PEG-PAsp (DET)-Chole solution into the DNA solution in the denaturation state such that the N/P ratio became 4, a polymer micelle complex of PEG-PAsp (DET)-Chole (hereinafter, "MCPM-2-GFP") encapsulating two linear single-stranded DNAs derived from one molecule of pGFP was formed. A 10 mM HEPES buffer (pH 7.3) was used as a reaction solvent. The pDNA concentration of the reaction solution was set as 100 ng/μL.

(3) Pancreatic Cancer Model Mice

As pancreatic cancer model mice, model mice to which human pancreatic adenocarcinoma cell line BxPC3 was transplanted to their pancreas were used.

The pancreatic cancer model mice were obtained as follows. First, BALB/c mice (obtained from Charles River Laboratories Inc.) were subcutaneously inoculated with BxPC3 (1×10⁷ cells) suspended in 100 μL PBS (Phosphate-buffered saline). The tumor progressed and entered the proliferation period (the size of the tumor was approximately 75 mm³) after 10 days.

(4) Systemic Administration to Pancreatic Cancer Mice

The polymer micelle complexes (injection volume: 200 ILL, DNA concentration: 100 ng/μL) produced in (1), (2), and (4) of Example 1 described above were injected to each pancreatic cancer model mouse from the tail veins. Pancreatic cancer tissues with which BxPC3 was transplanted were surgically cut out from the mice after 72 hours passed from the injection, the tissues were frozen in dried and cooled acetone, and thin layer sections having a thickness of 10 μm were prepared using a cryostat. In the obtained sections, cell nuclei were stained with Hoecst33342. Further, vascular endothelial cells were stained using an anti-mouse PECAM-1 antibody (manufactured by BD Pharmingen Inc.) and an anti-human and anti-mouse VEGFR1 antibody (product No: ab32152, manufactured by Abcam Japan).

Figure 5:
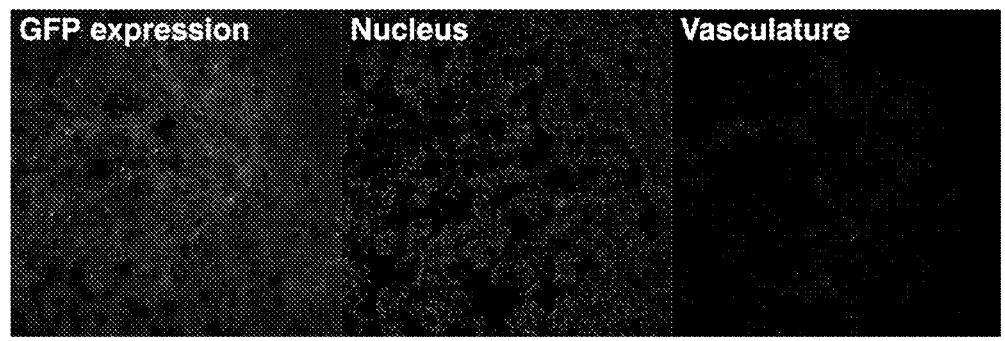
FIG. 5 shows fluorescence images of pancreatic cancer tissues of a mouse to which a polymer micelle complex MCPM-2-GFP is systemically administered in Example 2.
Figure 6:
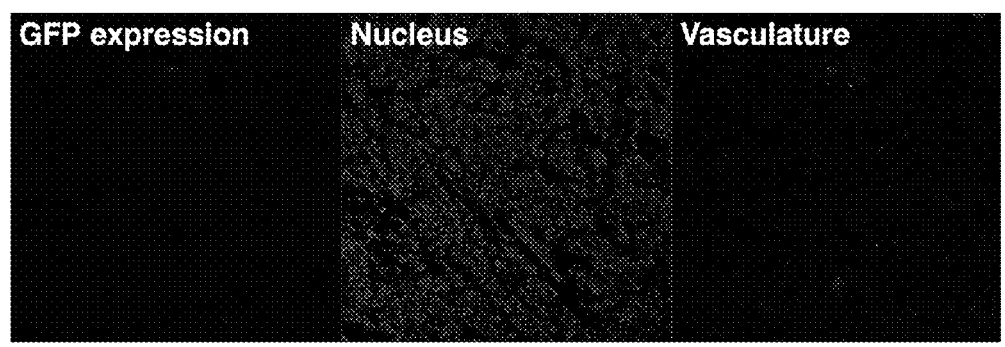
FIG. 6 shows fluorescence images of pancreatic cancer tissues of a mouse to which a polymer micelle complex PM-2-GFP is systemically administered in Example 2.
Figure 7:
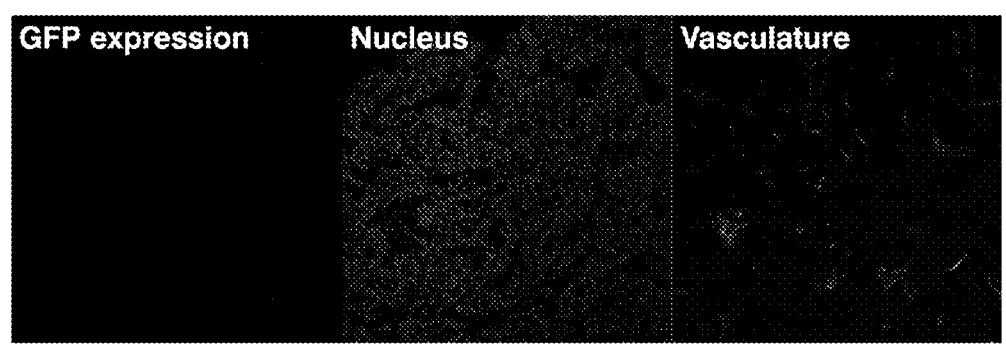
FIG. 7 shows fluorescence images of pancreatic cancer tissues of a mouse to which a polymer micelle complex MCPM-1 is systemically administered in Example 2.

After cells were stained, cells in which GFP expression was observed were only some of the entire tissues in the pancreatic cancer tissues of the mice to which the PM-2-GFP was systemically administered when the cells were observed using a confocal fluorescence microscope (product No: CLSM780, manufactured by Carl Zeiss). Meanwhile, in the pancreatic cancer tissues of mice to which MCPM-2-GFP was systemically administered, GFP expression was observed in an extremely large amount of cells even in the deep portions of tumor tissues. FIGS. 5 to 7 show fluorescence images captured by a fluorescence microscope. FIG. 5 shows fluorescence images of pancreatic cancer tissues of a mouse to which the MCPM-2-GFP was systemically administered. FIG. 6 shows fluorescence images of pancreatic cancer tissues of a mouse to which the PM-2-GFP was systemically administered. FIG. 7 shows fluorescence images of pancreatic cancer tissues of a mouse to which the MCPM-1 was systemically administered.

Figure 8:
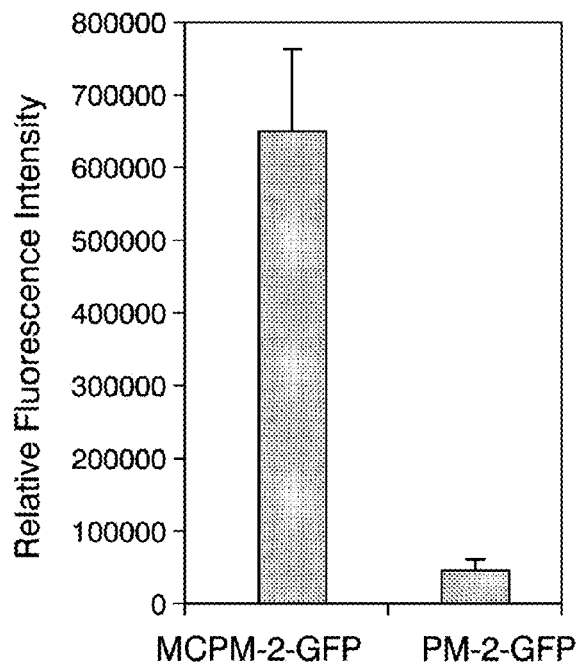
FIG. 8 is a diagram showing results of measurement of relative fluorescence intensity of GFP expression in deep portions of pancreatic cancer tissues of the pancreatic cancer model mouse to which the PM-2-GFP is administered and the pancreatic cancer model mouse to which the MCPM-2-GFP is administered among polymer micelle complexes accommodating GFP genes in Example 2.

The fluorescence intensity (brightness of an image) of GFP expressed in the pancreatic cancer tissues to which BxPC3 was transplanted was measured from the fluorescence images and the average value of eight images from which the backgrounds were subtracted was calculated as the fluorescence intensity. The results of measurement performed on the mice to which the PM-2-GFP was administered and the mice to which the MCPM-2-GFP was administered were shown in FIG. 8. In the mice to which the MCPM-2-GFP was administered, the GFP expression in the deep portion of tumor tissues of pancreatic cancer was 10 times or greater than the GFP expression in the deep portion thereof of the mice to which the PM-2-GFP was administered.

Example 3

The influence of the presence or absence of crosslinking of cationic polymer chain blocks on the retention in blood in a case of systemic administration of a nucleic acid-encapsulating polymer micelle complex was examined.

when the PDP group was reduced by dithiothreitol (DTT). The degrees of substitution acquired by two different methods coincide with each other and it was shown that the PDP groups were introduced to approximately 12% of amino groups of repeating units derived from lysine.

Before the obtained PEG-PLys-PDP was bonded to DNA and a polymer micelle complex was formed, DTT was added to the PEG-PLys-PDP in advance such that the concentration thereof became three times the concentration of the PDP group and then the mixture was stirred for 15 minutes and then the PDP group was reduced to thiol residues.

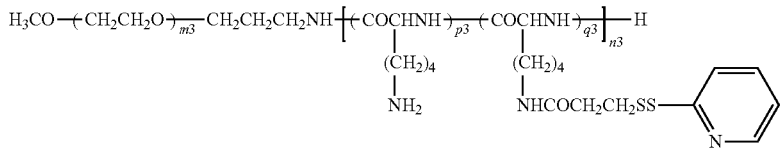

(1) PEG-PLys-PDP

A PEG-PLys (TFA) was prepared by performing ring-opening polymerization of an NCA using α-methoxy-ω-amino PEG (PEG Mw=20 kDa) as an initiator in the same manner as in (1) of Reference Example 1. At this time, three kinds of PEG-PLys' (TFA) with different polymerization degrees from each other were prepared by adjusting the ratio of the initiator to NCA, which is a monomer. The TFA group of three kinds of PEG-PLys' (TFA) obtained in the above-described manner was deprotected, thereby obtaining three kinds of PEG-PLys' whose polymerization degrees ("n2" in the following formula) were respectively 20, 40, and 70.

Next, a pyridyldithiopropyl group (PDP group) was introduced to the PEG-PLys. The introduction was performed using N-succinimidyl 3-(2-pyridyldithio)propionate (SPDP). The bromate salt of PEG-PLys was dissolved in 0.1 N acetate buffer having a pH value of 6.5 and was dialyzed against the same buffer, and thereby exchanging counterions to acetate ions. PEG-PLys acetate (200 mg) and SPDP (56 mg, 0.5 molar equivalent with respect to lysine residues) were dissolved in 5 mL of N-methylpyrrolidone (NMP, 5 mass % lithium chloride was added and degassed). 0.5 mL of N,N-diisopropylethylamine was added to this solution in order to deprotonate amines and the reaction was started. The reaction solution was stirred at room temperature for 1 hour and the reaction was tracked using reverse phase chromatography.

After the reaction finished, the reaction solution was added dropwise to and reprecipitated in ether, which is a poor solvent of PEG. After the crude product was dissolved in methanol, the operation of reprecipitation in ether was repeated and impurities insoluble in water were removed. Excessive salts were removed by dissolving the product in a 0.1 N acetic acid aqueous solution and being dialyzed against distilled water for 1 hour. The final purified product was freeze-dried and collected.

The structure of the obtained polymer was confirmed by $^1$H-NMR measurement. The degree of substitution of a PDP group was determined by $^1$H-NMR measurement and UV measurement. In the $^1$H-NMR measurement, the degree of substitution was acquired from the intensity ratio of peaks of protons ($C_3H_4N$: 7.6 ppm) of a pyridyl group in the PDP group to protons ($OCH_2CH_2$: 3.5 ppm) of a methylene group of PEG using $D_2O$ as a solvent. In the UV measurement, the degree of substitution was acquired from the absorbance ($\lambda_{max}$=343 nm, ε=7.06×10$^3$) of 2-thiopyridone separated (2) Formation of Uncrosslinked Nucleic Acid-encapsulating Polymer Micelle Complex Encapsulating Fluorescence-labeled pDNA after Denaturation A plasmid pCAG-Luc2 labeled by a fluorescent substance Cy (registered trademark) 5 used in Reference Example 1 was subjected to a restriction enzyme treatment, and then the pCAG-Luc2 was formed to have a linear shape through one site digestion. A DNA solution containing this linear DNA was subjected to a heat treatment at 95° C. for 10 minutes and the linear fluorescence-labeled pCAG-Luc2 was denatured to be single-stranded. Next, by rapidly mixing the PEG-PLys-PDP solution prepared in (1) described above after the reduction treatment was performed thereon into the DNA solution in the denaturation state such that the N/P ratio became 2, a polymer micelle complex of PEG-PLys-PDP (hereinafter, those using polymers in which the polymerization degrees of repeating units derived from lysine were 20, 40, and 70 were respectively referred to as "MCPM-3-PLys20," "MCPM-3-PLys40," and "MCPM-3-PLys70") encapsulating two linear single-stranded DNAs derived from one molecule of fluorescence-labeled pCAG-Luc2 was formed. A 10 mM HEPES buffer (pH 7.3) was used as a reaction solvent. The pDNA concentration of the reaction solution was set as 100 ng/μL.

(3) Formation of Nucleic Acid-encapsulating Polymer Micelle Complex which Encapsulates Fluorescence-labeled pDNA after Denaturation and in which Block Copolymers are Cross-Linked The reaction solution containing the polymer micelle complex formed in (2) described above was dialyzed against 1 L of a 10 mM phosphate buffer (pH 7.4) using a dialysis membrane having a cut-off molecular weight of 6000 to 8000 and DTT or the like was removed. The dialysis was continued for 3 days, thiol was oxidized by oxygen in air to form an SS bond, and crosslinking occurred therein. After three days of dialysis, absence of unoxidized thiol was confirmed by an Ellman method. MCP-3-PLys20 in which crosslinking occurred was referred to as MCPM-3-PLys20-CL, MCPM-3-PLys40 in which crosslinking occurred was referred to as MCPM-3-PLys40-CL, and MCPM-3-PLys 70 in which crosslinking occurred was referred to as MCPM-3-PLys70-CL.

(4) Evaluation of Retention in Blood

The polymer micelle complexes (injection amount: 200 μL, DNA concentration: 100 ng/μL) formed in (2) and (3)

described above were injected to mice from the side tail veins. Each polymer micelle complex was respectively administered to four mice. The blood was collected from venae cavae of the mice after 30 minutes from the administration and the serum was prepared by performing a centrifugation treatment. Trypsin and dextran sulfate were added to the obtained serum and the serum was incubated overnight at 37° C. The fluorescence intensity (670 nm) of Cy (registered trademark) 5 of incubated serum was measured using a fluorescence spectrophotometer (product name: Nano Drop (ND-3300), manufactured by Wilmington Corporation).

The ratio (%) of the amount of a polymer micelle complex staying in the blood of a mouse to the total amount thereof after 30 minutes from the systemic administration was calculated by the following formula. In the formula, "$F_{670}$ (sample)" means a measured value of the fluorescence intensity at 670 nm of the serum (after incubation with trypsin and dextran sulfate) prepared from a mouse to which a polymer micelle complex was administered. Further, "$F_{670}$ (control)" means a measured value of the fluorescence intensity at 670 nm of a serum, wherein the serum was prepared from a mouse to which a polymer micelle complex was not administered yet, and the serum was added a polymer micelle complex with the same amount as that of the polymer micelle complex administered to the mouse to form a control serum, further added trypsin and dextran sulfate and incubated overnight at 37° C. in the same manner as that of the sample.

[Ratio (%) of amount of polymer micelle complex staying in blood]=[$F_{670}$ (sample)]/[$F_{670}$ (control)]×100

Figure 9:
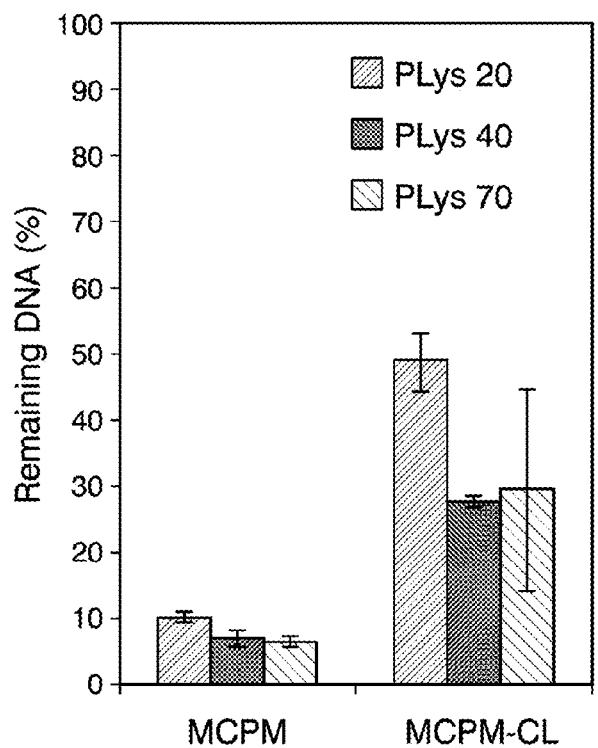
FIG. 9 is a diagram showing measurement results of the ratio (%) of the amount of a polymer micelle complex remaining in the blood after 30 minutes from systemic administration with respect to the total amount of the polymer micelle complex systemically administered to a mouse in Example 3.

The measurement results are shown in FIG. 9. In FIG. 9, "MCPM" shows results of mice to which "MCPM-3-PLys20," "MCPM-3-PLys40," and "MCPM-3-PLys70" were administered and "MCPM-CL" shows results of mice to which "MCPM-3-PLys20-CL," "MCPM-3-PLys40-CL," and "MCPM-3-PLys70-CL" were administered. When a block copolymer was crosslinked, the retention in blood was remarkably improved.

Example 4

Using plasmid (pVenus, 5.5 kbp) containing genes coding green fluorescent protein Venus, Venus gene-encapsulating polymer micelle complexes were produced according to a conventional method that allows pDNA to be incorporated as it is and a method that allows pDNA to be bonded to a block copolymer in a state in which the double helix structure of pDNA is dissociated. Further, the complexes were systemically administered to model mice having pancreatic cancer and Venus expression in pancreatic cancer tissues was examined. In addition, the pVenus was obtained by incorporating genes coding Venus in the plasmid pCA-GGS (provided from RIKEN Gene Bank).

(1) PEG-PLys-PDP

A PEG-PLys (TFA) was prepared by performing ring-opening polymerization of an NCA using α-methoxy-ω-amino PEG (PEGS Mw=20 kDa) as an initiator in the same manner as in (1) of Reference Example 1. At this time, three kinds of PEG-PLys' (TFA) with different polymerization degrees from each other were prepared by adjusting the ratio of the initiator to NCA, which is a monomer. The TFA group of three kinds of PEG-PLys' (TFA) obtained in the above-described manner was deprotected, thereby obtaining PEG-PLys whose polymerization degree was 72.

Subsequently, a PDP group was introduced to the obtained PEG-PLys in the same manner as in (1) of Example 3. When the structure of the obtained polymer was confirmed by $^1$H-NMR measurement, the PDP group was introduced to approximately 12% of amino groups of repeating units derived from lysine.

Before the obtained PEG-PLys-PDP was bonded to DNA and a polymer micelle complex was formed, DTT was added to the PEG-PLys-PDP in advance such that the concentration thereof became three times the concentration of the PDP group and then the mixture was stirred for 15 minutes and then the PDP group was reduced to thiol residues.

(2) cRGD-PEG-PLys-PDP

Cyclic RGD peptide (cRGD) is a ligand that selectively recognizes αvβ3 and αvβ5 integrins over-expressed in tumor cells and tumor vascular endothelial cells, cRGD-PEG-PLys-PDP in which cRGD was introduced to the terminal of a PEG block was synthesized.

Specifically, acetyl-PEG-PBLA-Chole was obtained in the same manner as in (1) of Example 1 except that α-acetyl-ω-amino PEG (PEG, Mw=20 kDa) was used as an initiator in place of α-methoxy-ω-amino PEG The obtained acetyl-PEG-PBLA-Chole was dissolved in water, the pH thereof was adjusted to pH2 using hydrochloric acid, and then an acetyl group was completely converted into an active aldehyde group (acidified acetyl-PEG-PBLA-Chole solution)

Alternatively, cyclo{(RGDfk(CX-)}peptides were dissolved in a sodium hydrogen carbonate buffer (0.1 N, pH7.4) containing DTT having 10 times equivalent of peptides in order to cut off an SS bond which may be formed among these peptides and then incubated for 1 hour (cRGD peptide solution).

Subsequently, the cRGD peptide solution was added to the acidified acetyl-PEG-PBLA-Chole solution such that the RGD peptide became 10 times equivalent of the acetyl-PEG-PBLA-Chole, and the solution was adjusted to have a pH value of 5 and reacted overnight. cRGD-PEG-PAsp (DET)-Chole which was a final reaction product was dialyzed three times in a 1M sodium chloride aqueous solution and dialyzed three times with deionized water.

(3) Formation of Nucleic Acid-encapsulating Polymer Micelle Complex Encapsulating pVenus as it is A polymer micelle complex of the PEG-PLys-PDP encapsulating pVenus (hereinafter, "PM-4-Venus") was formed by rapidly mixing a plasmid pVenus solution into the PEG-PLys-PDP solution produced in (1) described above such that the N/P ratio became 2. A 10 mM HEPES buffer (pH 7.3) was used as the reaction solvent. The plasmid concentration of the reaction solution was set as 100 ng/µL.

Next, the reaction solution containing the formed polymer micelle complex was dialyzed for 3 days in the same manner as in (3) of Example 3, thiols in the polymer micelle complex were oxidized to an SS bond and then cross-linked. The resultant obtained through the crosslinking was set as PM-4-Venus-CL.

(4) Formation of Nucleic Acid-encapsulating Polymer Micelle Complex Encapsulating pVenus after Denaturation The pVenus was subjected to a restriction enzyme treatment and then formed to have a linear shape through one site digestion. A DNA solution containing this linear DNA was subjected to a heat treatment at 95° C. for 10 minutes and the linear fluorescence-labeled pVenus was denatured to be single-stranded. Next, by rapidly mixing the PEG-PLys-PDP solution prepared in (1) described above after the reduction treatment was performed thereon into the DNA solution in the denaturation state such that the N/P ratio became 2, a polymer micelle complex of PEG-PLys-PDP (hereinafter, "MCPM-4-Venus") encapsulating two linear single-stranded DNAs derived from one molecule of pVenus was formed. A 10 mM HEPES buffer (pH 7.3) was used as a reaction solvent. The pDNA concentration of the reaction solution was set as 100 ng/μL.

Next, the reaction solution containing the formed polymer micelle complex was dialyzed for 3 days in the same manner as in (3) of Example 3, and thiols in the polymer micelle complex were oxidized to an SS bond and then cross-linked. The resultant obtained through the crosslinking was referred to as MCPM-4-Venus-CL.

(5) Formation of Nucleic Acid-encapsulating Polymer Micelle Complex which Encapsulates pVenus after Denaturation and to which cRGD is Introduced Cross-linked MCPM-4-Venus-C L-cRGD encapsulating two linear single-stranded DNAs derived from one molecule of pVenus was obtained in the same manner as in (4) described above except that the cRGD-PEG-PLys-PDP solution prepared in (2) described above after the reduction treatment was performed thereon was used in place of the PEG-PLys-PDP solution prepared in (1) described above after the reduction treatment was performed thereon.

(6) Systemic Administration to Pancreatic Cancer Mice

The polymer micelle complexes (injection volume: 200 μL, DNA concentration: 100 ng/μL) produced in (3), (4), and (5) described above were injected to the same pancreatic cancer model mice used in (3) of Example 2 from the tail veins respectively. Pancreatic cancer tissues with which BxPC3 was transplanted were surgically cut out from the mice after 72 hours passed from the injection in the same manner as in (4) of Example 2, sections for microscopic observation were prepared, and cell nuclei and vessels in the obtained sections were fluorescence-stained.

Figure 10:
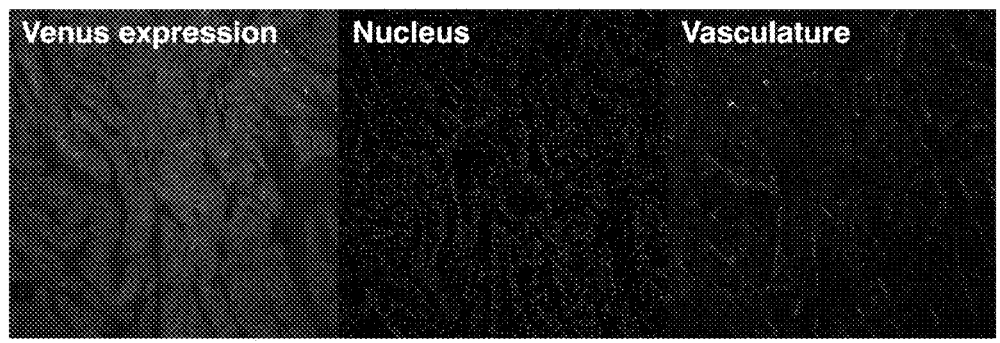
FIG. 10 shows fluorescence images of pancreatic cancer tissues of a mouse to which a polymer micelle complex (MCPM-4-Venus-CL) is systemically administered in Example 4.

After cells were stained, cells in which Venus expression was observed were only some of the entire tissues in the pancreatic cancer tissues of the mice to which the PM-4-Venus-CL, encapsulating pVenus as it was, was systemically administered when the cells were observed using a confocal fluorescence microscope. Meanwhile, in the pancreatic cancer tissues of mice to which MCPM-4-Venus-CL, encapsulating pVenus after denaturation, was systemically administered. Venus expression was observed in an extremely large amount of cells even in the deep portions of tumor tissues. Further, in the pancreatic cancer tissues of mice to which MCPM-4-Venus-CL-cRGD to which cRGB ligand was added was systemically administered, Venus expression was observed in a large amount of cells similar to the MCPM-4-Venus-CL. FIG. 10 shows fluorescence images of pancreatic cancer tissues of a mouse to which the MCPM-4-Venus-CL is systemically administered.

Example 5

PEG-PLys-PDP (PEG-PLys20-SH10%) in which the polymerization degree was and the degree of substitution of a PDP group was 10% and PEG-PLys-PDP (PEG-PLys69-SH12%) in which the polymerization degree was 69 and the degree of substitution of a PDP group was 12% were produced in the same manner as in (1) of Example 3. Before these block copolymers were bonded to DNA and a polymer micelle complex was formed, DTT was added thereto in advance such that the concentration thereof became three times the concentration of the PDP group and then the mixture was stirred for 15 minutes and then the PDP group was reduced to thiol residues.

Next, a plasmid pCAG-Luc solution was mixed into these block copolymer solutions and a polymer micelle complex of PEG-PLys-PDP encapsulating pCAG-Luc was formed in the same manner as in (3) of Example 1.

Figure 11:
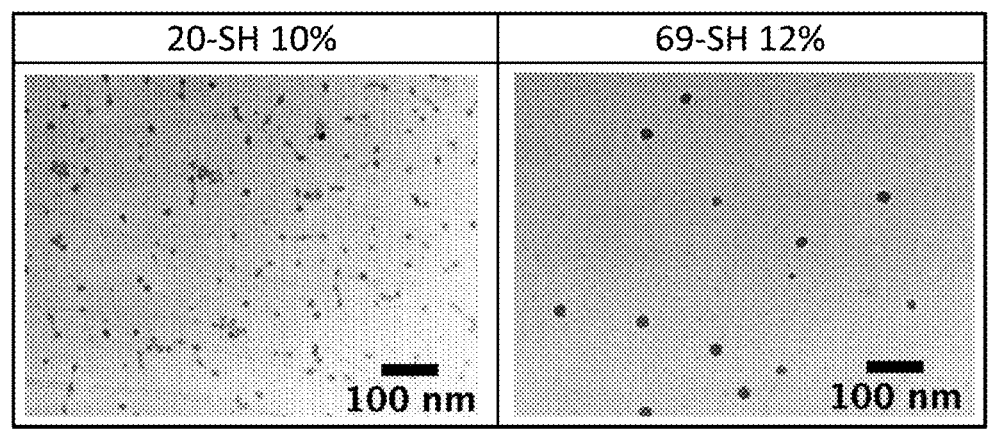
FIG. 11 shows TEM images of respective polymer micelle complexes in Example 5.

TEM images of the obtained polymer micelle complexes were imaged in the same manner as (6) of Reference Example 1. FIG. 11 respectively shows a TEM image of a polymer micelle complex using PEG-PLys20-SH10% (left, "20-SH10%") and a TEM image of a polymer micelle complex using PEG-PLys69-SH12% (right, "69-SH12%"). In the case of the polymer micelle complex using PEG-PLys20-SH10%, two cores clearly smaller than those of the polymer micelle complex using PEG-PLys69-SH12% were paired with each other. The PEG density of a shell portion of the polymer micelle complex using PEG-PLys20-SH1100% was clearly higher than that of the polymer micelle complex using PEG-PLys69-SH12%. From these results, in the polymer micelle complex using PEG-PLys20-SH10%, it was assumed that each of two single-stranded DNAs derived from pCAG-Luc was individually condensed and paired with each other. Since DNA strands were entangled with each other even after a heat treatment, the DNA strands were not able to be completely separated from each other even after condensation so that the DNAs were paired with each other. In other word, in the polymer micelle complex using PEG-PLys69-SH12%, it is considered that two single-stranded DNAs derived from pCAG-Luc were contained in one core.

Example 6

The influence of the presence or absence of crosslinking of cationic polymer chain blocks on the form of a nucleic acid-encapsulating polymer micelle complex was examined.

PEG-PLys in which the polymerization degree was 21 and PEG-PLys-PDP in which the polymerization degree was 21 and the degree of substitution of a PDP group was 12% were produced in the same manner as in (1) of Example 3. Before the block copolymer of PEG-PLys-PDP was bonded to DNA and a polymer micelle complex was formed, DTT was added thereto in advance such that the concentration thereof became three times the concentration of the PDP group and then the mixture was stirred for 15 minutes and then the PDP group was reduced to thiol residues.

Next, a plasmid pCAG-Luc2 solution was mixed into these block copolymer solutions and a polymer micelle complex of PEG-PLys encapsulating pCAG-Luc2 (hereinafter, "MCPM-6") and a cross-lined polymer micelle complex of PEG-PLys-PDP (hereinafter, "MCPM-6-CL") which encapsulates pCAG-Luc2 were formed in the same manner as in (2) and (3) of Example 3.

Figure 12:
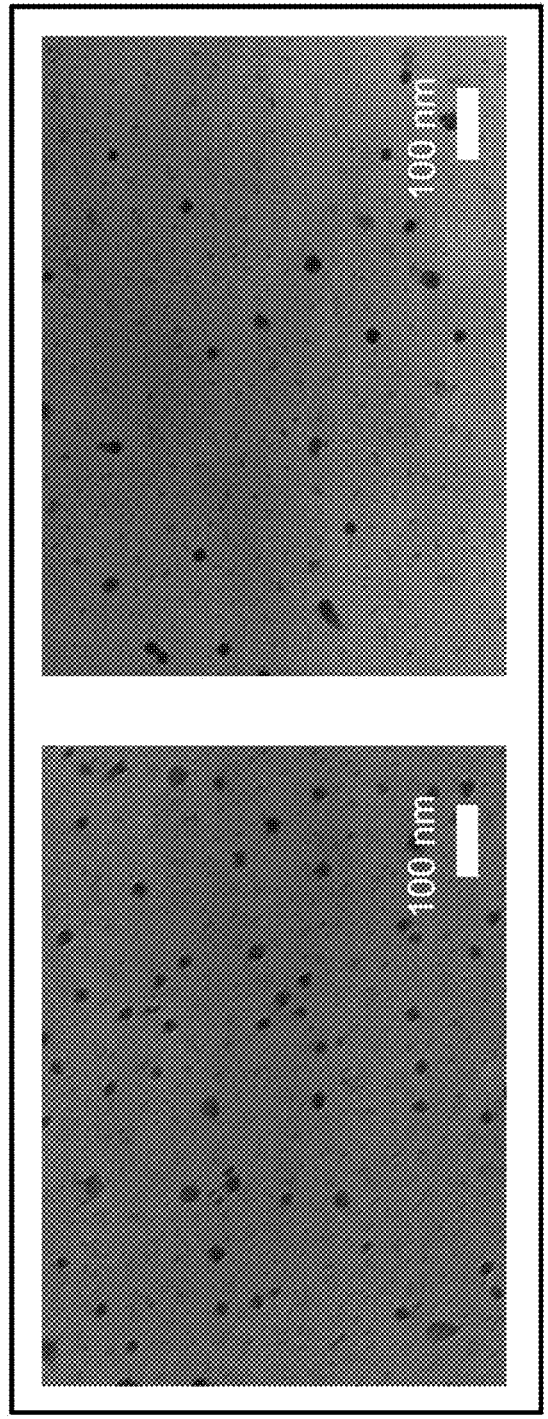
FIG. 12 shows TEM images of respective polymer micelle complexes in Example 6.
Figure 13:
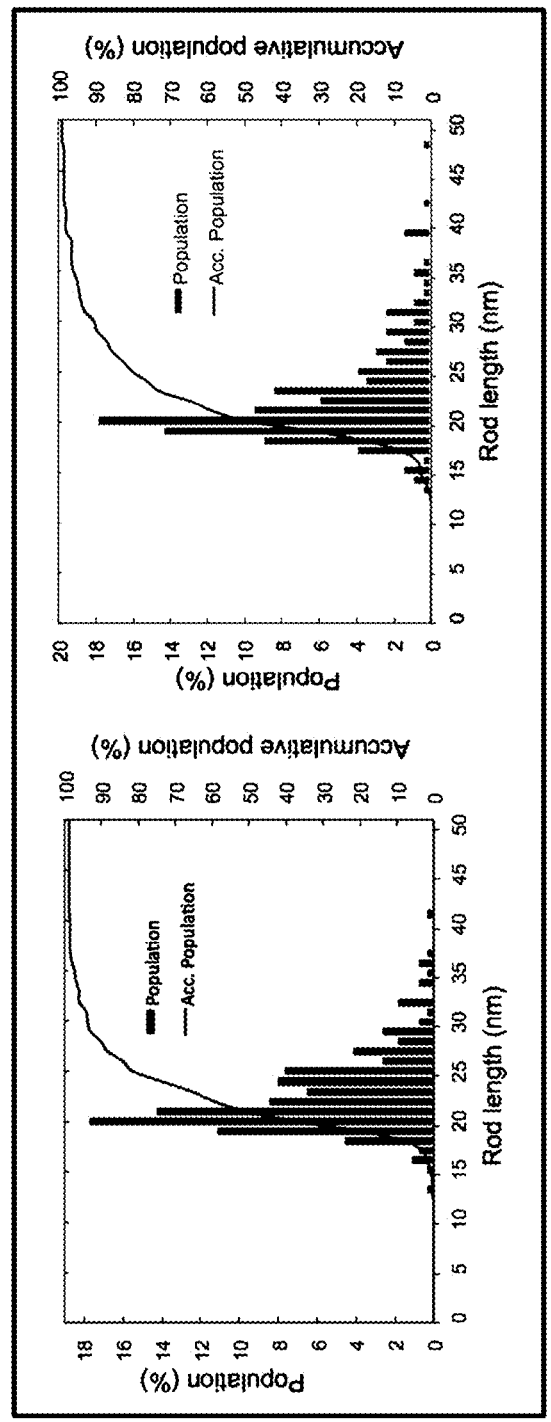
FIG. 13 are diagrams showing distribution of long axis lengths of polymer micelle complexes calculated from the TEM images of the respective polymer micelle complexes in Example 6.

TEM images of the obtained polymer micelle complexes were imaged in the same manner as (6) of Reference Example 1. FIG. 12 respectively shows a TEM image (left) of a polymer micelle complex using PEG-PLys (MCPM-6) and a TEM image (right) of a polymer micelle complex using PEG-PLys-PDP (MCPM-6-CL). In addition, FIG. 13 shows distribution of long axis lengths of polymer micelle complexes calculated from the images. As a result, a difference in the form of a core portion of a polymer micelle complex due to the presence or absence of crosslinking was not found and it was understood that crosslinking had no influence on the form of a core portion of a polymer micelle complex.

Example 7

The influence of the nucleic acid denaturation temperature on the size and the form of a nucleic acid-encapsulating polymer micelle complex was examined.

PEG-PLys whose polymerization degree was 21 was produced in the same manner as in Example 6.

Next, a polymer micelle complex of the PEG-PLys encapsulating pCAG-Luc2 was formed in the same manner as in Example 6 except that a heat treatment of a linear DNA solution was performed at a temperature of 25° C., 70° C., 80° C., or 95° C. for 10 minutes.

Figure 14:
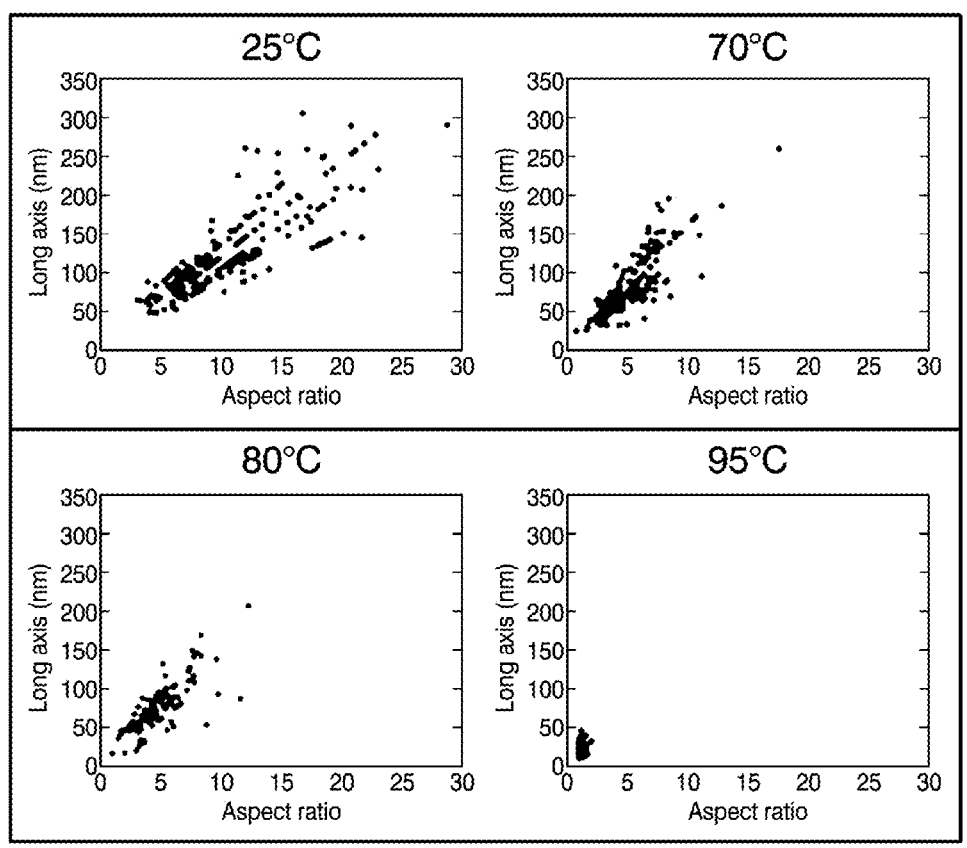
FIG. 14 is diagrams showing distribution of long axis lengths and aspect ratios of a polymer micelle complex subjected to a denaturing treatment at respective temperatures in Example 7.

A TEM image of the obtained polymer micelle complex was imaged in the same manner as in (6) of Reference Example 1 and distribution based on the long axis lengths and the aspect ratios of the polymer micelle complex which were calculated from the obtained image was examined. The results are shown in FIG. 14. As a result, it was understood that both of the long axis length and the aspect ratio became smaller by performing a heat treatment at a temperature (70° C. or higher) equal to or higher than room temperature and dispersion among polymer micelle complexes decreased. Particularly, it was understood that a polymer micelle complex population having a small particle diameter and small dispersion was obtained by performing a heat treatment at 95° C.

Example 8

Gene transfer to a cultured cell line using a nucleic acid-encapsulating micelle complex was examined.

First, cell line BxPC-3 derived from human pancreatic cancer adenocarcinoma was liquid-cultured at 12000 cells/well ($3\times10^4$ cells/mL in a culture of 400 µL/well) using 24 well plates. RPMI-1640 containing 10% fetal bovine serum (FBS) and 5% penicillin/streptomycin was used as a culture medium. After culture of the cell line at 37° C. for 24 hours, six samples for each kind were transfected using 30 µL (33 ng/µL) of a polymer micelle complex (hereinafter, "MCPM-8") solution of PEG-PLys72 (polymerization degree of PLys block: 72) or a cross-linked polymer micelle complex (hereinafter. "MCPM-8-CL") solution of PEG-PLys69-SH12 obtained in the same manner as in (1) of Example 3. HEPES was used as a control.

Figure 15:
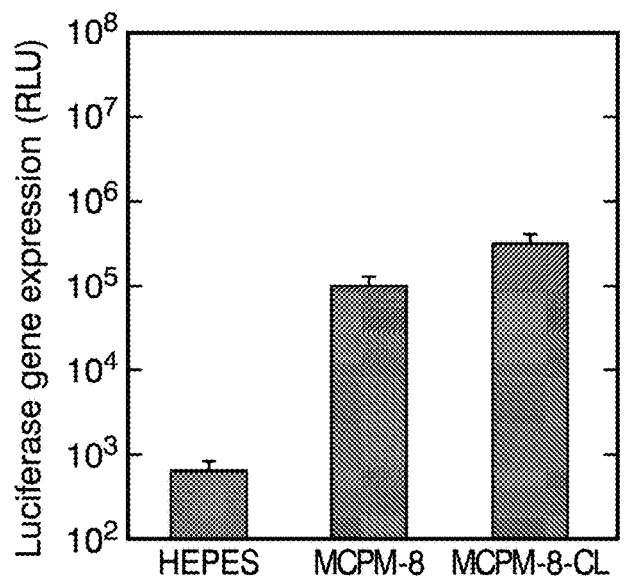
FIG. 15 is a diagram showing measurement results of relative fluorescence intensity of luciferase expression in a cell line into which PEG-PLys or PEG-PLys-PDP accommodating luciferase genes is transfected in Example 8.

After 24 hours, the media were exchanged and then the samples were cultured for 3 days. Thereafter, the samples were washed with a PBS solution three times and collected using a 150 µL passive lysis buffer. Using a 40 µL lysate, luciferase gene expression was quantified by GloMax™ 96 Microplate Luminomater using fluorescence intensity from which the background was subtracted. The results are shown in FIG. 15.

From the result, it is understood that the polymer micelle complex of the present invention is introduced to human cultured cell lines regardless of the presence or absence of crosslinking and genes contained in the polymer micelle complex are expressed in human culture cell lines.

Example 9

(1) PEG-PLys-PDP

PEG-PLys-PDP in which the polymerization degree was 21 and the degree of substitution of a PDP group was 12% were produced in the same manner as in (1) of Example 4. Before the block copolymer of PEG-PLys-PDP was bonded to DNA and a polymer micelle complex was formed, DTT was added thereto in advance such that the concentration thereof became three times the concentration of the PDP group and then the mixture was stirred for 15 minutes and then the PDP group was reduced to thiol residues.

(2) Formation of Nucleic Acid-encapsulating Polymer Micelle Complex Encapsulating pCAG-sFlt-1 after Denaturation Plasmid pCAG-sFlt-1 was prepared by incorporating sFlt-1 genes in the plasmid pCAGGS (provided from RIKEN Gene Bank). It is considered that the sFlt-1 genes inhibit angiogenesis by antagonizing a vascular endothelial cell growth factor receptor (VEGFR) involved in angiogenesis and have anti-tumor effects. The obtained pCAG-sFlt-1 was subjected to a restriction enzyme treatment and then formed to have a linear shape through one site digestion. A DNA solution containing this linear DNA was subjected to a heat treatment at 95° C. for 10 minutes and the linear pCAG-sFlt-1 was denatured to be single-stranded.

Moreover, by rapidly mixing a linear pCAG-sFlt-1 solution denatured to be single-stranded into the PEG-PLys-PDP solution produced in (1) described above such that the NIP ratio became 2, a polymer micelle complex of PEG-PLys-PDP (hereinafter, "MCPM-9-sFlt1-PDP") encapsulating two linear single-stranded DNAs derived from one molecule of plasmid pCAG-sFlt-1 was formed. A 10 mM HEPES buffer (pH 7.3) was used as a reaction solvent. The pDNA concentration of the reaction solution was set as 100 ng/µL.

Next, the reaction solution containing the formed MCPM-9-sFlt1-PDP was dialyzed for 3 days in the same manner as in (3) of Example 3, and thiols in the polymer micelle complex were oxidized to an SS bond and then cross-linked. The resultant obtained through the crosslinking was set as MCPM-9-sFt1-CL.

A polymer micelle complex (hereinafter, "PM-9-sFlt1-CL") obtained in the same manner as in (2) described above except that the pCAG-sFlt-1 was not denatured by a heat treatment and a polymer micelle complex (hereinafter, "MCPM-9-Luc2-CL") obtained in the same manner as in (2) described above except that Luc2 genes were incorporated in place of sFlt-1 genes using the same method as in Reference Example 1 were formed as controls.

(3) Systemic Administration to Pancreatic Cancer Mice

Any of the three polymer micelle complexes produced in (2) described above or HEPES was injected to the same pancreatic cancer model mice used in (6) of Example 3 from the tail veins respectively three times in total (0-th day, third day, sixth day) in an amount of 200 µm (plasmid or pDNA concentration: 100 ng/µL) for each time every two days.

Figure 16:
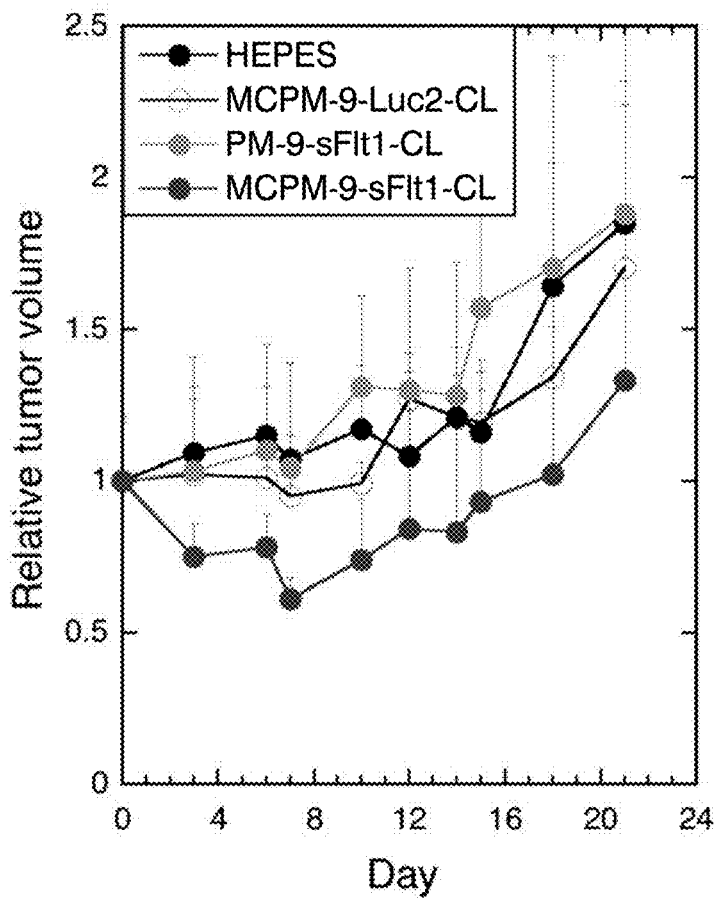
FIG. 16 is a diagram showing results of measurement of the size of pancreatic cancer in a mouse to which respective polymer micelle complexes are systemically administered in Example 9.

The results of measuring the volumes of pancreatic cancer of mice for 22 days are shown in FIG. 16. From the results, it is understood that tumor growth in mice is effectively suppressed by administering "MCPM-9-Flt1-CL."

INDUSTRIAL APPLICABILITY

Since the nucleic acid-encapsulating polymer micelle complex according to the present invention has a small particle diameter and the density of the uncharged hydrophilic polymer chain block constituting a shell portion of the nucleic acid-encapsulating polymer micelle complex is high, retention in blood, tumor vascular permeability, and tumor tissue penetrability are excellent. For this reason, in the nucleic acid-encapsulating polymer micelle complex according to the present invention, DNA encapsulated therein can be efficiently introduced to a deep portion of cancer tissues through systemic administration such as intravenous administration. Therefore, the nucleic acid-encapsulating polymer micelle complex according to the present invention is not particularly limited, but is extremely useful as a gene carrier for delivering therapeutic genes to target cells. The nucleic acid-encapsulating polymer micelle complex of the present invention can be used in the pharmaceutical or medical industry. For example, according to the present invention, it is expected that gene therapy becomes possible through systemic administration to refractory cancer with lower vascular permeability.

The invention claimed is:

1. A method for producing a nucleic acid-encapsulating polymer micelle complex which accommodates DNA, the method comprising:
   a process of mixing a block copolymer containing an uncharged hydrophilic polymer chain block and a cationic polymer chain block with double-stranded DNA of 1000 or more base pairs in a state in which at least a part of the double-stranded DNA is denatured in an aqueous medium;
   wherein the double-stranded DNA has been denatured at 80° C. or higher prior to the process of mixing with the block copolymer, and
   the complex is spherical and has diameters having a ratio of a longest diameter to another diameter of 1:1.

2. The method for producing a nucleic acid-encapsulating polymer micelle complex according to claim 1, wherein the double-stranded DNA is 2000 or more base pairs in length.

3. The method for producing a nucleic acid-encapsulating polymer micelle complex according to claim 1, wherein the double-stranded DNA is linear.

4. The method for producing a nucleic acid-encapsulating polymer micelle complex according to claim 1, wherein the average particle diameter thereof in an aqueous medium measured according to a dynamic light scattering method is 100 nm or less.

5. The method for producing a nucleic acid-encapsulating polymer micelle complex according to claim 1,
   wherein the DNA and the cationic polymer chain block bonded to the DNA due to an electrostatic interaction form a core portion, and
   the uncharged hydrophilic polymer chain block forms a shell portion.

6. The method for producing a nucleic acid-encapsulating polymer micelle complex according to claim 5,
   wherein the average particle diameter of the core portion is 50 nm or less.

7. The method for producing a nucleic acid-encapsulating polymer micelle complex according to claim 1,
   wherein at least a part of the block copolymer is mutually cross-linked.

8. The method for producing a nucleic acid-encapsulating polymer micelle complex according to claim 1,
   wherein a hydrophobic group is covalently bonded to a main chain or a side chain of the cationic polymer chain block.

9. The method for producing a nucleic acid-encapsulating polymer micelle complex according to claim 1,
   wherein the cationic polymer chain block has an ethylamine structure or a propylamine structure in the side chain thereof.

* * * * *